US011826167B2

(12) United States Patent
Turner

(10) Patent No.: US 11,826,167 B2
(45) Date of Patent: *Nov. 28, 2023

(54) SYSTEMS AND METHODS OF TREATING PROPRIOCEPTIVE DYSFUNCTION AND VESTIBULAR DISORDERS

(71) Applicant: James Walter Turner, McKinney, TX (US)

(72) Inventor: James Walter Turner, McKinney, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/902,983

(22) Filed: Sep. 5, 2022

(65) Prior Publication Data

US 2022/0409131 A1 Dec. 29, 2022

Related U.S. Application Data

(63) Continuation of application No. 16/657,940, filed on Oct. 18, 2019, now Pat. No. 11,432,764.

(51) Int. Cl.
*A61B 5/00* (2006.01)
*A61B 5/11* (2006.01)
(Continued)

(52) U.S. Cl.
CPC .............. *A61B 5/6801* (2013.01); *A61B 5/11* (2013.01); *A61B 5/4023* (2013.01);
(Continued)

(58) Field of Classification Search
CPC ............................................ A63B 21/02–0557
See application file for complete search history.

(56) References Cited

U.S. PATENT DOCUMENTS 4,910,802 A * 3/1990 Malloy .............. A63B 21/4009
2/69
5,109,546 A * 5/1992 Dicker ............... A41D 13/0015
482/121

(Continued)

FOREIGN PATENT DOCUMENTS

EP           3808416 A1 * 4/2021   ......... A41D 13/1281
WO    WO-2014/020627 A1    2/2014
WO    WO-2015/138515 A1    9/2015

OTHER PUBLICATIONS

European Patent Office, Communication, Extended European Search Report issued for European Patent Application No. 20202603.5, dated Mar. 15, 2021, 7 pages.

*Primary Examiner* — Nyca T Nguyen
(74) *Attorney, Agent, or Firm* — Norton Rose Fulbright US LLP

(57) ABSTRACT

The systems, methods, apparatuses, and articles disclosed herein provide a new approach to treatment symptoms, such as proprioceptive dysfunction and vestibular disorders, which may be caused by certain types of human ailments. According to the present disclosure, a wearable article may include one or more limb sections and a resilient member may be provided along a length of each of the one or more limb sections and configured to generate a resistance force. Adjustments to the resistance force provided by the resilient member(s) may be adjusted using cord locks. As a user wearing the wearable article moves, the resistance force is applied to the user's limbs. Strain gauges may be provided to measure the resistance force(s), which enables verification that the resilient members are sized and configured to provide an appropriate amount of resistance force to a user and may improve programs and regimens designed to treat such ailments.

20 Claims, 12 Drawing Sheets

(51) Int. Cl.
*A63B 21/055* (2006.01)
*A63B 21/00* (2006.01)
*A63B 21/04* (2006.01)
*A63B 23/035* (2006.01)
*H04W 4/80* (2018.01)

(52) U.S. Cl.
CPC ...... *A63B 21/0428* (2013.01); *A63B 21/0557* (2013.01); *A63B 21/4025* (2015.10); *A63B 23/035* (2013.01); *A61H 2201/1657* (2013.01); *A63B 2220/833* (2013.01); *H04W 4/80* (2018.02)

(56) References Cited

U.S. PATENT DOCUMENTS

| | | | | |
|---|---|---|---|---|
| 5,308,305 | A * | 5/1994 | Romney | A63B 21/4021 482/121 |
| 5,737,773 | A | 4/1998 | Dicker et al. | |
| 6,179,760 | B1 * | 1/2001 | Rumbaugh | A41D 31/18 482/121 |
| 6,248,043 | B1 | 6/2001 | Morton | |
| 7,931,571 | B2 | 4/2011 | Bernardoni | |
| 8,641,652 | B2 | 2/2014 | Gazayerli | |
| 10,857,414 | B1 * | 12/2020 | Lopez | A63B 21/4035 |
| 11,173,090 | B2 * | 11/2021 | Dellacqua | A61F 5/02 |
| 11,331,529 | B1 * | 5/2022 | Cranke | A63B 21/4021 |
| 11,432,764 | B2 * | 9/2022 | Turner | A63B 23/035 |
| 2002/0160891 | A1 | 10/2002 | Gallagher | |
| 2004/0204302 | A1 | 10/2004 | Flynn | |
| 2010/0204014 | A1 | 8/2010 | Hoffman | |
| 2011/0209264 | A1 * | 9/2011 | Williams | A41D 13/0015 2/69 |
| 2011/0230314 | A1 | 9/2011 | Hoffman et al. | |
| 2012/0123310 | A1 * | 5/2012 | Gazayerli | A61H 1/0292 602/36 |
| 2013/0067628 | A1 * | 3/2013 | Harb | A63B 21/00061 2/69 |
| 2013/0085040 | A1 | 4/2013 | Bowers | |
| 2015/0190669 | A1 * | 7/2015 | Matsuura | A63B 21/4039 482/8 |
| 2015/0258362 | A1 * | 9/2015 | Cornish | A63B 21/4017 482/8 |
| 2015/0306441 | A1 * | 10/2015 | Yao | A63B 21/4019 482/124 |
| 2016/0317853 | A1 * | 11/2016 | Benocci | A63B 21/4025 |
| 2017/0028244 | A1 * | 2/2017 | Schreiber | A63B 21/4025 |
| 2017/0361151 | A1 * | 12/2017 | Mottern | A41D 13/0015 |
| 2018/0184735 | A1 | 7/2018 | Longinotti-Buitoni et al. | |
| 2018/0236308 | A1 | 8/2018 | Hyde et al. | |
| 2019/0054338 | A1 * | 2/2019 | Tang | A63B 23/03533 |
| 2019/0134454 | A1 | 5/2019 | Mahoney et al. | |
| 2019/0269967 | A1 * | 9/2019 | Thomas | A63B 21/00185 |
| 2022/0133198 | A1 * | 5/2022 | Popov | A61B 5/224 73/379.01 |

* cited by examiner

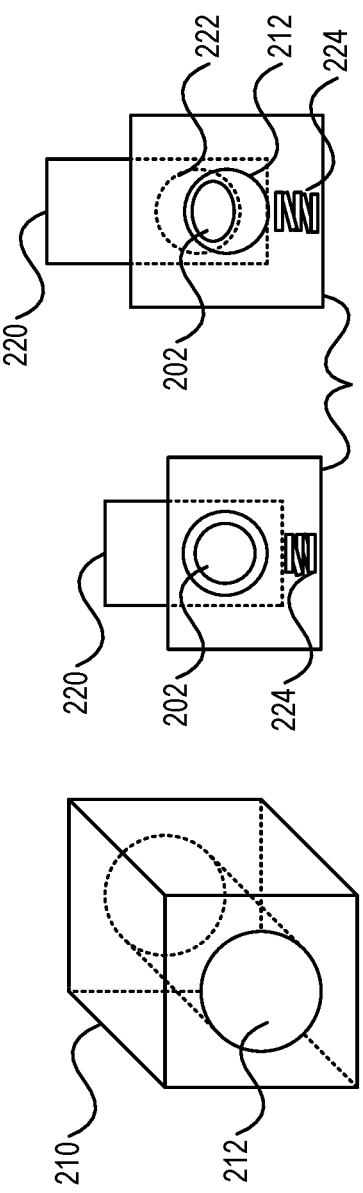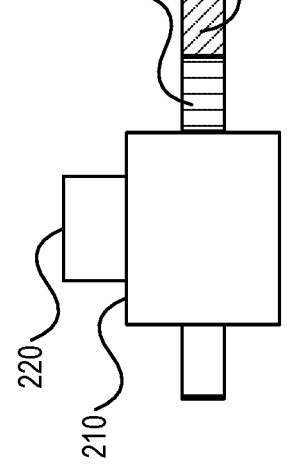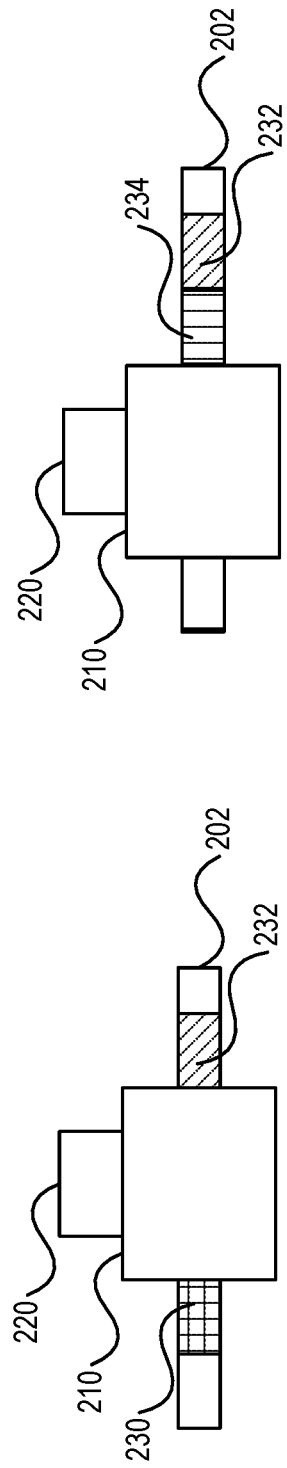

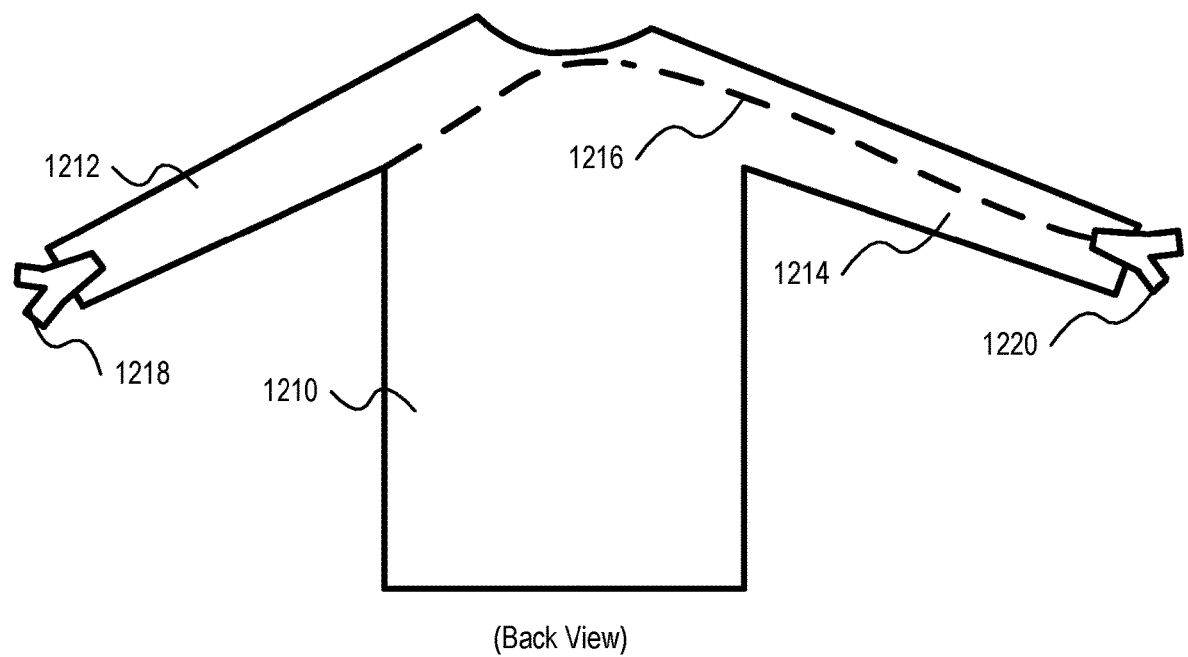
(Back View)
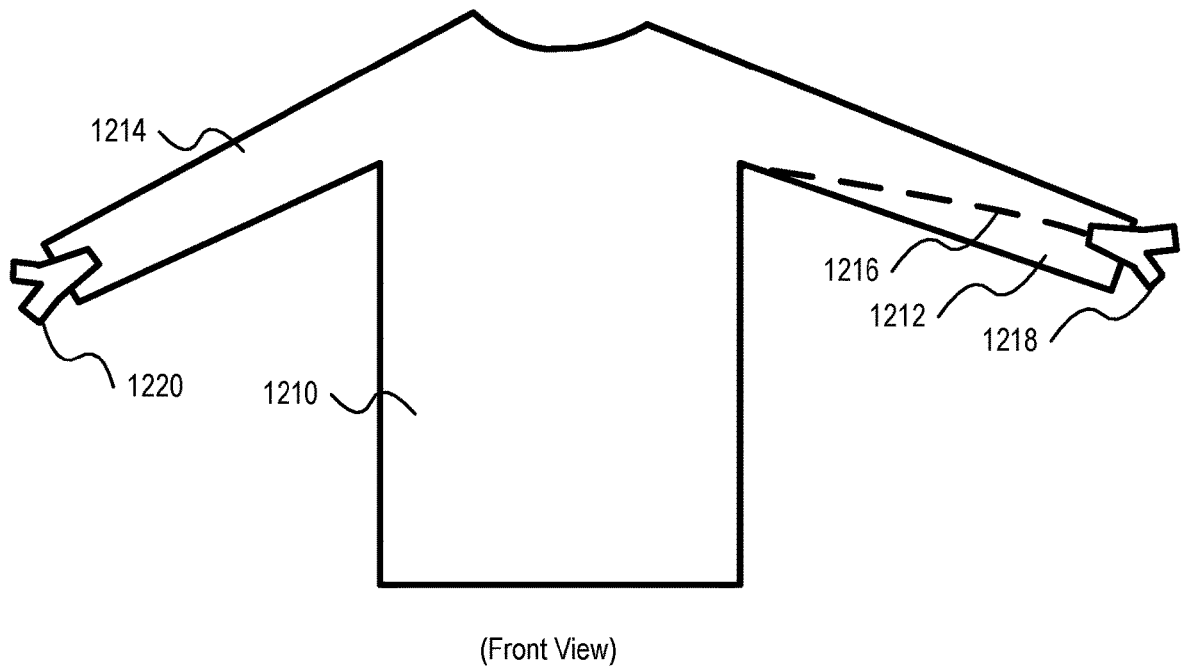
(Front View)
FIG. 12

SYSTEMS AND METHODS OF TREATING PROPRIOCEPTIVE DYSFUNCTION AND VESTIBULAR DISORDERS

CROSS-REFERENCE TO RELATED APPLICATION

The present application is a continuation of U.S. patent application Ser. No. 16/657,940 filed Oct. 18, 2018 and entitled "SYSTEMS AND METHODS OF TREATING PROPRIOCEPTIVE DYSFUNCTION AND VESTIBULAR DISORDERS," the disclosure of which is incorporated by reference herein in its entirety.

TECHNICAL FIELD

The present disclosure relates to medical treatment devices and more specifically to rehabilitation and exercise devices, systems, and methods configured to address ailments caused by proprioceptive dysfunction and vestibular disorders.

BACKGROUND

The proprioceptive sense refers to the sensory input and feedback that tells the human body about movement and body position and could be considered the "position sense." This sensory input and feedback is provided when receptors (i.e., proprioceptors) located throughout the muscles, joints, ligaments, tendons, and connective tissues of the human body are activated. However, some persons suffer from proprioceptive dysfunction, which manifests itself in a variety of ways. For example, persons suffering from proprioceptive dysfunction may appear clumsy or uncoordinated or may have difficulty performing basic or normal tasks/activities.

Proprioceptive dysfunction occurs when the proprioceptive sense does not receive or interpret input correctly within these muscles and joints. When proprioceptive input is not received correctly, it is often the result of a lack of proper messages being provided by the receptors, such as providing a proper indication that muscles are being stretched, joints are bending or straightening, and/or how much of each of these actions is happening (e.g., how far muscles are being stretched or joints are being bent/straightened). Persons suffering from proprioceptive dysfunction may often exhibit the following "clinical" signs: postural stability, motor planning, grading movement, and motor control.

Another ailment is vestibular disorders or balance disorders. Vestibular disorders can cause dizziness, vertigo, imbalance, problems with hearing, nausea, fatigue, anxiety, problems with concentration, and other symptoms. For example, such a disorder may cause a person to have poor balance and spatial orientation, which may cause difficulty maintaining a straight posture, cause vertigo and dizziness (e.g., the sensation of being pulled in one direction), or cognitive and psychological difficulties, such as concentrating and emotional maturity. These symptoms can significantly impact a person's day-to-day functioning, ability to work, social relationships, and quality of life.

SUMMARY

In the description below, embodiments providing systems, methods, articles of manufacture, and apparatuses configured to address at least some of the various ailments described above are disclosed. In an exemplary embodiment, a wearable article is provided and includes various features configured to aid in the treatment of the aforementioned ailments. The wearable article may include one or more limb sections (e.g., one or more legs of a pair of pants, one or more sleeves of a shirt, etc.). The one or more limb sections may include a resilient member disposed along a length of the one or more limb sections, such as along a sideseam of a sleeve or pant leg, along an inseam of the pant leg or sleeve, or both the sideseam and the inseam. The resilient member may be a shock cord or some other material designed to stretch when appropriate force is applied and then return to its original form when the force is released.

An appropriately sized resilient member may be provided for the one or more limb sections, such as by attaching first and second ends of the resilient member to the limb section(s) (e.g., by sewing the first end of the resilient member to a first end of a limb section and sewing the second end of the resilient member to a second end of the limb section). However, in some instances, dynamically adjustable resilient members may be provided. For example, a cord lock may be provided on one end of the resilient member and the cord lock may be configured to slideably engage the resilient member. To facilitate the slidable engagement of the cord lock to the resilient member, the cord lock may include a housing having a hole sized to allow the resilient member to be passed through it. A locking mechanism may be configured to lock the cord lock at a desired position along the length of the resilient member, such as by applying a pinching force that prevents the resilient member from being advanced through or pulled out of the hole of the cord lock housing.

The resilient member may be configured to provide or create a desired amount of resistance force. For example, the wearable article may be worn by a user and as the user moves around, the limb section corresponding to the resilient member may be moved causing the resilient member to stretch, creating the desired amount of resistance force. The resilient member(s) may include a plurality of indicators designed to identify locations where the cord lock should be positioned to ensure the appropriate amount of force is provided by the resilient member.

In addition to the wearable article described above, a system facilitating monitoring of a user's utilization of the wearable article is disclosed. The system may include one or more strain gauges (e.g., one strain gauge for each resilient member). The one or more strain gauges may be configured to determine an amount of strain placed on the resilient member, which may indicate the amount of resistance force provided by the resilient member. The strain gauge may be configured to provide information regarding the measured strain of the resilient member(s) to a remote device. To facilitate the providing of the information to the remote device, a communication interface may be provided with or integrated with the wearable article. The communication interface may be communicatively coupled with the one or more strain gauges and may receive information associated with a resistance force provided by the resilient member(s) associated with each strain gauge. Once received from the strain gauge, the communication interface may transmit the resistance force information to the remote device for presentation via a graphical user interface. The presentation of the resistance information at the graphical user interface of the remote device may facilitate various types of monitoring of the system, such as to verify that the resilient members are properly engaged with the cord locks and that the resilient member(s) is providing the correct resistance force. Additionally, the monitoring may enable the progress of the user to be tracked and adjustments to be made as the user improves in one or more areas relevant to the aforementioned ailments.

The wearable article and system briefly described above are configured to addresses various affliction commonalities. One such affliction is postural stability (e.g., the ability to hold and maintain one's postural muscles and responses), which may improve one's sense of security and safety during movement. For example, children with proprioceptive dysfunction may be unable to move and use their body effectively, which may cause them to become easily frustrated, give up, lose self-confidence and experience an impaired sense of "emotional security." Another affliction addressed by embodiments of the present disclosure is motor planning (e.g., conceptualizing and figuring out what each part of one's body needs to do in order to move a certain way or complete a task, also referred to as "grading movement".) Embodiments may enable the user to learn how much pressure is needed to complete a task (e.g., hold a cup of water, hold and write with a pencil, turn the page of a book, hit a golf ball into the hole, etc.) By treating such afflictions with the wearable articles, systems, and methods disclosed herein, the users' ability to overcome these ailments and improve their quality of life may be realized and the negative impact that proprioceptive dysfunction and vestibular disorders have may be mitigated.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the disclosed methods and apparatuses, reference should be made to the embodiments illustrated in greater detail in the accompanying drawings, wherein:

FIG. 2A is a block diagram illustrating aspects of a cord lock housing in accordance with the present disclosure;

FIG. 2B is a block diagram illustrating additional aspects of a cord lock housing in accordance with the present disclosure;

FIG. 2C is a block diagram illustrating additional aspects of a cord lock housing in accordance with the present disclosure;

FIG. 2D is a block diagram illustrating aspects of configuring a resistance force in accordance with the present disclosure;

FIG. 2E is a block diagram illustrating additional aspects of configuring a resistance force in accordance with the present disclosure;

FIG. 12 is a block diagram illustrating a wearable article configured in accordance with embodiments of the present disclosure for training a golf swing.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION

Figure 1:
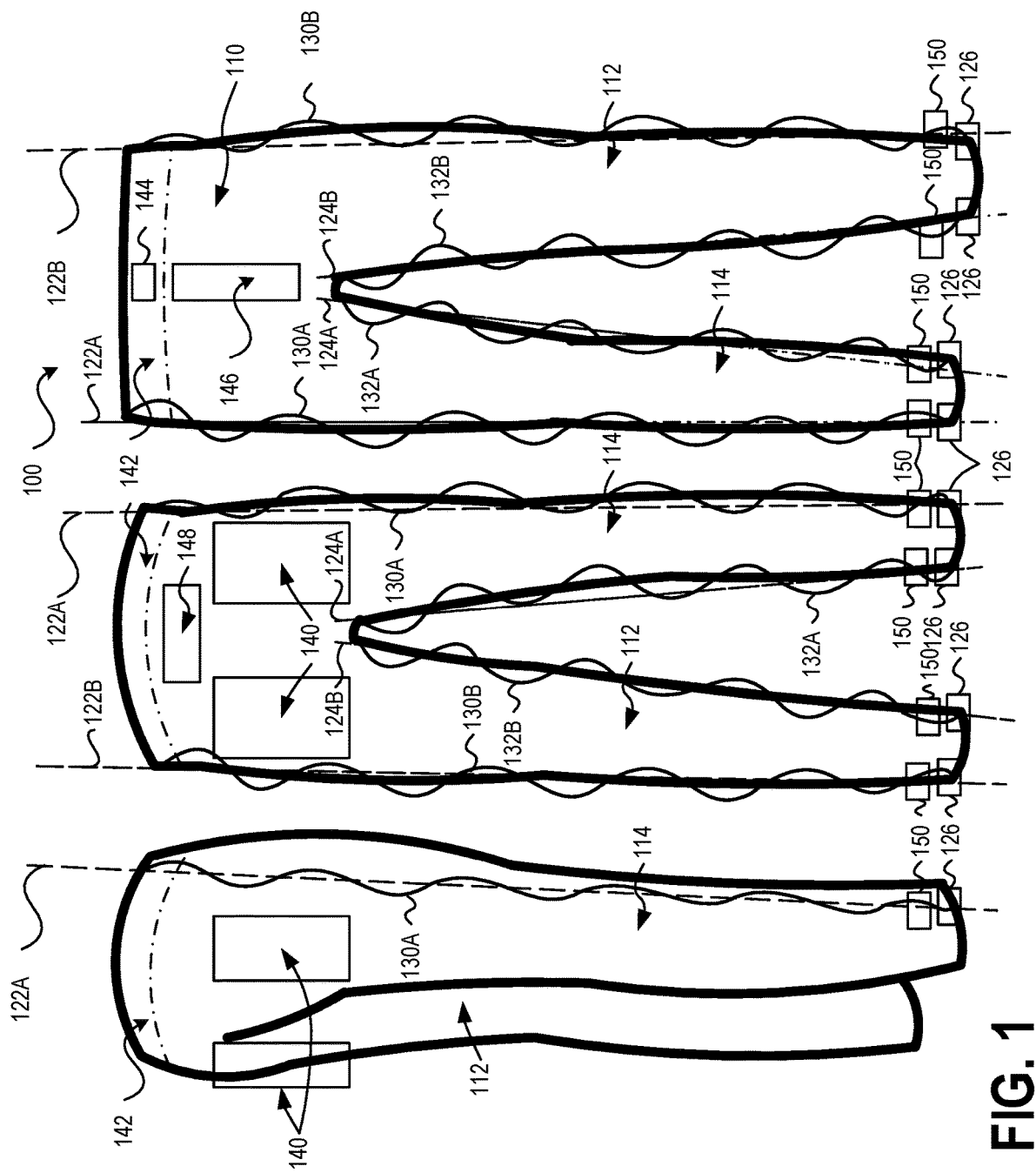
FIG. 1 is a diagram illustrating aspects of a wearable article for treating proprioceptive dysfunction and vestibular disorders in accordance with the present disclosure.
Figure 3:
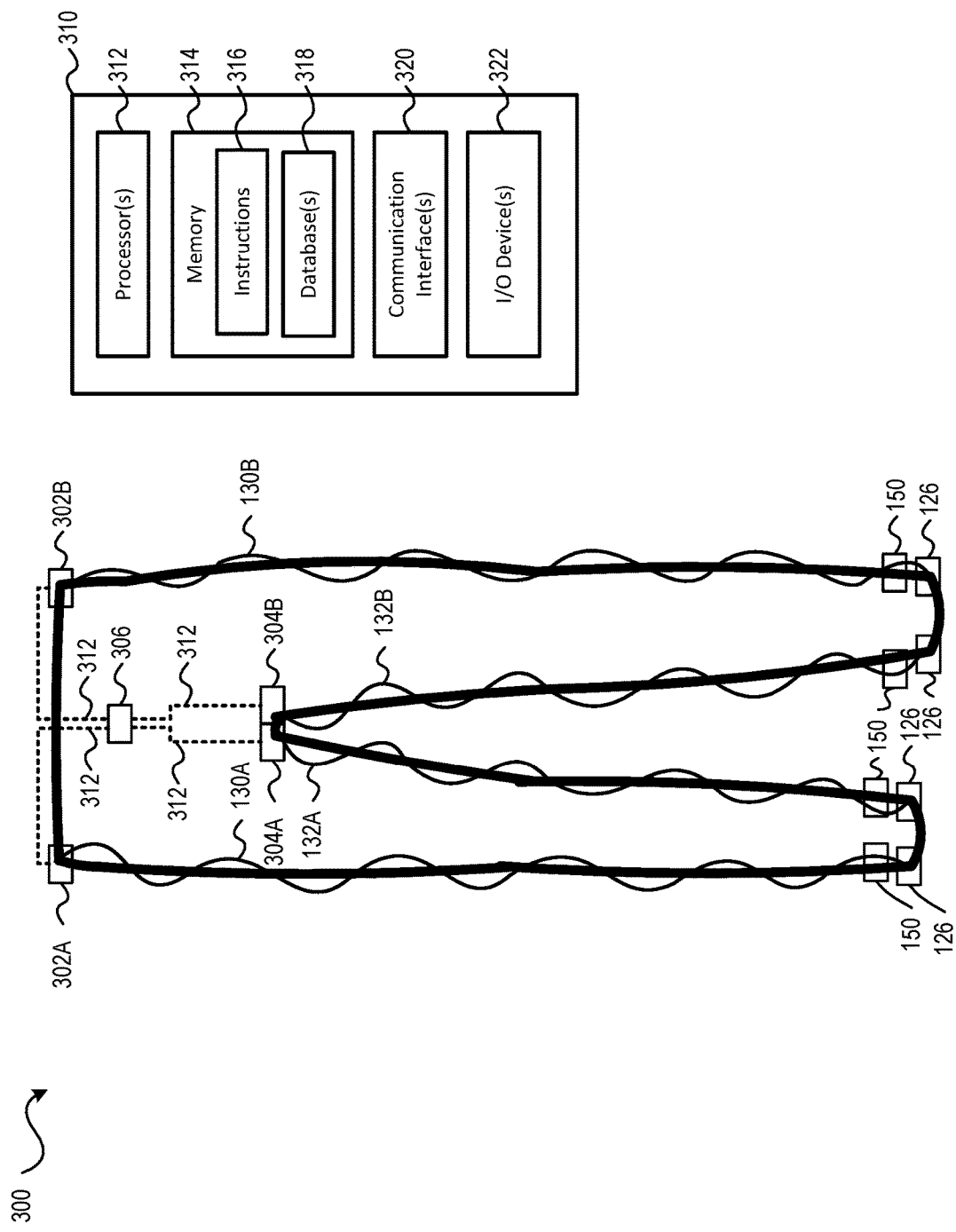
FIG. 3 is a block diagram of a system for treating proprioceptive dysfunction and vestibular disorders in accordance with the present disclosure.

Referring to FIG. 1, a diagram illustrating aspects of a wearable article for treating proprioceptive dysfunction and vestibular disorders in accordance with the present disclosure is shown as a wearable article 100. It is noted that although FIGS. 1 and 3 illustrate the wearable article as a pair of pants, such disclosure has been provided for purposes of illustration only, rather than by way of limitation. Accordingly, it is to be understood that the concepts and structure of the wearable garment 100 of FIG. 1 and the wearable garment 300 of FIG. 3 could be adapted to other types of wearable garments, such as a long sleeve shirt, a short sleeve shirt, shorts, an arm or leg sleeve, a sweatshirt, gloves, forearm garments (with or without gloves), hooded shirts (to address neck injuries), shoes, socks, calf sleeves, torso wraps (e.g., sleeveless garments for facilitating trunk monitoring), or other types of garments depending on the particular ailments to be addressed and the types of treatments to be provided.

As shown in FIG. 1, the wearable article 100 may be a pair of pants having a body portion or section 110, a first limb portion or section 112, and a second limb portion or section 114. When worn by a user, the user's waist and hips may be approximately located within the body portion 110, the user's left leg may be approximately located within the first limb portion 112, and the user's right leg may be approximately located within the second limb portion 114. The first limb portion 112 may include a sideseam 122B and an inseam 124B, and the second limb portion 114 may include a sideseam 122A and an inseam 124A. The sideseams 122A, 122B may extend along an outside length of the first limb portion 112 and the second limb portion 114, respectively, and the inseams 124A, 124B extend along an inside length of the first limb portion 112 and the second limb portion 114, respectively. It is noted that the inside length may be less than the outside length. The body portion 110 may optionally include a waistband region 142, a button or other fastener 144, a fly 146, and a back yoke region 148. The waistband region 142 may include one or more belt loops, an elastic band, a drawstring, or other features configured to maintain the wearable article appropriately situated on the user's body. The wearable article 100 may also include one or more pockets 140, which may include pockets disposed on a buttocks region of the body portion 110, as shown at 140, or pockets disposed on a front region of the body portion 110 (not shown in FIG. 1 for simplicity of the figure).

One or more resilient members may be provided at particular locations in order to aid in the treatment of one or more human ailments, such as proprioceptive dysfunction and vestibular disorders. For example, as shown in FIG. 1, a resilient member 130A may be provided along the length of the limb section 114 proximate to sideseam 122A, a resilient member 130B may be provided along the length of the limb section 112 proximate to sideseam 122B, a resilient member 132A may be provided along the length of the limb section 114 proximate to inseam 124A, and a resilient member 132B may be provided along the length of the limb section 112 proximate to inseam 124B. The resilient members 130A, 130B, 132A, 132B may be configured to generate a resistance force. For some applications of the wearable article 100, each of the resilient members 130A, 130B, 132A, 132B may be configured to generate the same resistance force. However, in other applications resilient members 130A, 130B, 132A, 132B may be configured to generate different resistance forces. Although FIG. 1 illustrates the resilient members 132A, 132B as extending along the length 124A, 12B, respectively, of the inseams of the wearable article 100, it is noted that resilient members 132A, 132B may, in some embodiments, extend beyond the inseams and be anchored proximate the waist region 142 or another location, such as a should harness or assembly (described in more detail below).

The utilization of resilient members that generate different resistance forces may aid in training the user to overcome ailments resulting from proprioceptive dysfunction or vestibular disorders. For example, the different resistance forces may simulate the forces experienced when the user feels off balance or may train the user to overcome the feeling of being off balance. The resistance training provided by the wearable article 100 aids in the development of muscle and connective tissue. Vestibular and proprioceptive training provided by embodiments of the present disclosure target brain development thereby increasing agility, balance and sense of movement. Applying specific and targeted resistance training to minor muscle groups allows medical professionals to get indications and exact readings for weak or injured muscle groups for additional muscle training or targeting nerve control areas. In addition to being used as a training device, physicians treating cerebral palsy patients may use the wearable article 100 as a monitoring device to track neuropathy across each specific muscle in the quadriceps group thereby mapping the movement and growth of nerve deterioration, where different resilient members of the wearable article 100 facilitate tracking of different muscles within the targeted muscle group. An occupational therapist might choose to monitor or treat a muscle group imbalance in a Downs Syndrome patient by first identifying the left gluteus muscle as a weak point requiring muscle development and adjusting the type of vestibular treatment once the muscle group of interest or treatment area of interest is identified.

In an embodiment, the resilient members 130A, 130B, 132A, 132B may be shock cords having a braided sheath that surrounds a stretchy core material, such as rubber or braided woven sheets. The resilient members 130A, 130B, 132A, 132B may have varying thicknesses, which may contribute to the resistance forces generated by the resilient members. For some applications, all of the resilient members may have a same thickness while other applications may involve different ones of the resilient members having different thicknesses. It is noted that the particular thicknesses and resistance forces utilized for a particular wearable article configured according to the present disclosure may vary depending on the type of treatment to be provided, characteristics of the patient, or other factors. For example, thicker resilient members configured to generate higher resistance forces may be utilized for wearable articles utilized to treat adults and thinner resilient members configured to generate lower resistance forces (e.g., relative to the resistance forces utilized to treat adults) may be utilized for children. In addition to the size or age of a patient, the configuration of a wearable article according to aspects of the present disclosure may also be determined according to a muscle group size and the type of treatment to be provided, as may be determined based on specifications of a medical professional. The wearable articles disclosed herein also provide consistent treatment for the patient. To illustrate, the disclosed wearable articles exhibit high levels of repeatability and consistency with respect to the treatment received by the patient, which may be attributed, at least in part, to the use of resilient members capable of providing consistent levels of resistance force over time.

Additionally, the disclosed wearable articles facilitate high levels of customization, allowing the treatments provided by the wearable articles to be tuned to specific needs and characteristics of each individual patient. Exemplary customizations include a strength of the resistance forces applied during treatment, the orientation at which the resistance forces are applied, the location(s) where the resistance forces are applied, the type of wearable article (e.g., pants, calf-sleeve, shirt, etc.) used to provide the treatment, and the like. These capabilities provide physicians with robust control over the treatment of the patient and the ability to customize treatment plans to meet the needs of each patient. For example, the physician may determine various aspects of the treatment (e.g., location of treatment, type of wearable article used to provide treatment, number of resilient members, position of the resilient members, resistance force provided by each resilient member, etc.) based on the needs of the patient and the patient's physical characteristics. Tuning the wearable article to the specifications and needs of an individual patient may also increase the effectiveness of the treatment. As an example, a physician may specify a configuration for a wearable article that includes 50 gauge resilient members configured to apply resistance forces to major muscle groups and four 8 gauge resilient members configured to facilitate measurements associated with hip flexor muscles, allowing different resistance forces to be targeted to different muscle groups and provide treatments specific to each targeted region of the body. Additionally, the wearable articles of embodiments may also include sensors that facilitate monitoring of the resistance forces and treatment of the patient by the physician, thereby enabling a complete treatment solution to be provided for the patient, as described in more detail below.

In embodiments, the number of resilient members provided for the wearable article 100 may vary. For example, a wearable article 100 may include a single resilient member (e.g., only one of the resilient members 130A, 130B, 132A, 132B) disposed on the first limb portion 112 or the second limb portion 114. As another example, a wearable article 100 may include a two resilient members (e.g., two of the resilient members 130A, 130B, 132A, 132B) disposed on a single limb portion (e.g., two resilient members on the first limb portion 112 or the second limb portion 114) or two resilient members disposed on the first and second limb portions 112, 114 (e.g., one resilient member disposed on the first limb portion 112 and a second resilient member disposed on the second limb portion 114). In some situations, resilient members may only be provided on the sideseam(s) of at least one limb portion and no resilient members may be provided at the inseam portions, while in other situations one or more resilient members may be provided at one or both of the inseams and no resilient members may be provided at the sideseams.

Figure 4:
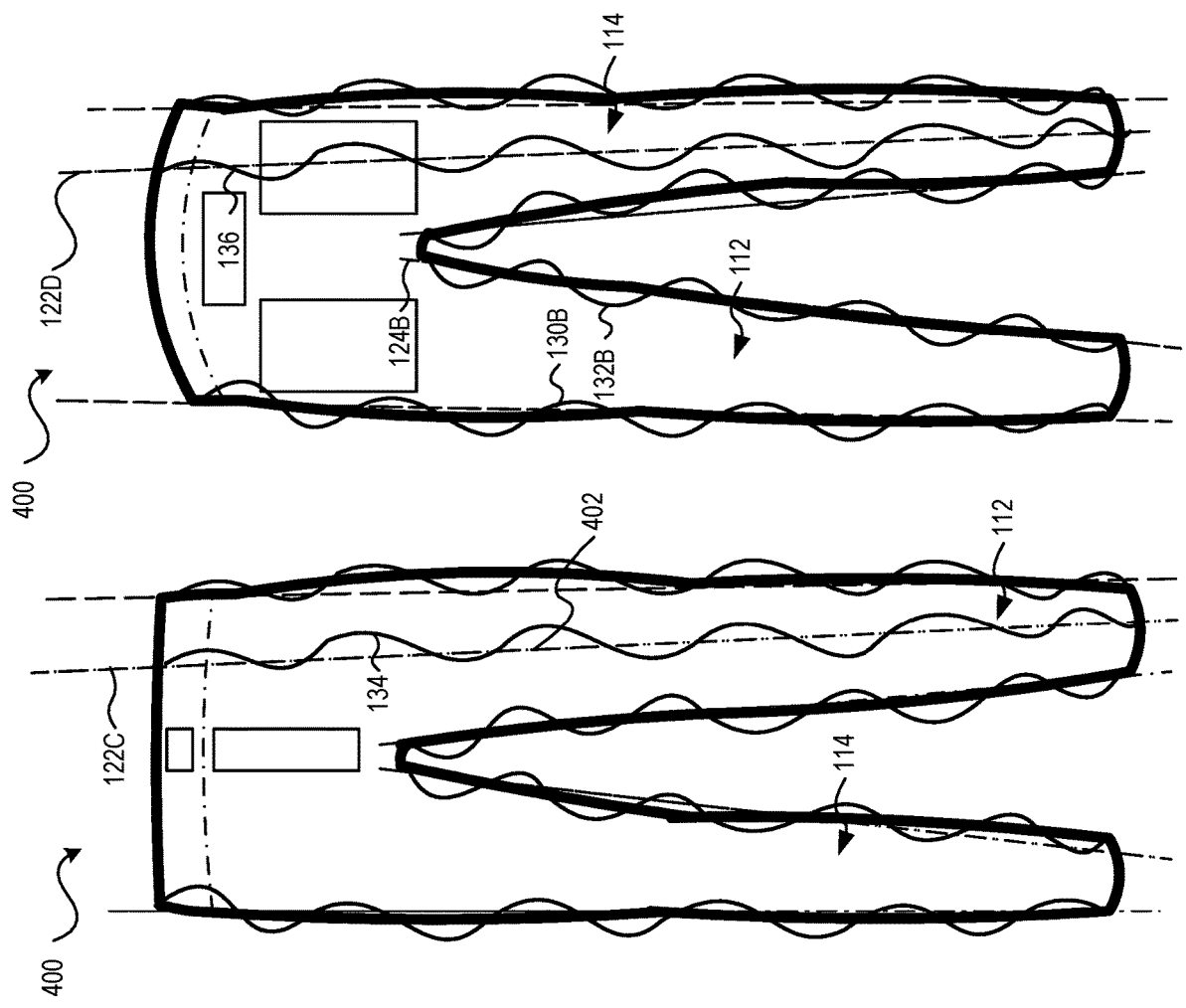
FIG. 4 is a block diagram illustrating additional aspects of a wearable article according to aspects of the present disclosure.

It is noted that the exemplary configurations described above have been provided for purposes of illustration, rather than by way of limitation and that other combinations of positions where resilient members are provided may be utilized depending on the particular needs/ailments of the user and the desired treatment regimen. For example and referring to FIG. 4, a block diagram illustrating additional aspects of a wearable article configured according aspects of the present disclosure is shown. As shown in FIG. 4, a wearable article 400 may include the resilient members described and illustrated with reference to FIG. 1, as well as additional resilient members 134 and 136, which may be disposed along a length of the front (e.g., 122C) or back (e.g., 122D) of a limb portion of the wearable article 400. The particular locations where the one or more resilient members are anchored with respect to the wearable article may vary depending on the particular treatment to be provided. For example, in FIG. 4, the resilient member 134 may be anchored at a first end along the length of the front of the limb portion 402 along path 122C at a location 402, which may approximate a position along the patient's thigh, and at a second end proximate the bottom portion of the limb section (e.g., proximate the area where the patient's foot or ankle would be located). Anchoring the resilient member 134 at particular locations may direct the resistance force provided by resilient member 134 towards a targeted muscle or muscle group of the patient, thereby allowing fine control over the treatment provided by the resistance forces generated during use of the wearable article. Additionally, resilient members may be anchored at locations such as the calf muscle (e.g., to apply the resistance force to the calf muscles) or other locations. Further, resilient members may be configured to generate resistance forces at various angles, such as by having a first end of a resilient member anchored to the back of the limb portion (e.g., a leg limb portion) and then wrapping around and down toward the foot to anchor a second end of the resilient member on the toe portion of a shoe (e.g., to treat or correct intoeing).

Referring back to FIG. 1, the resistance force generated by the resilient members may be tuned to provide a particular or desired resistance force. For example, the resilient members may include one or more resistance level indicators associated with specific resistance forces. Cord locks may be provided to adjust a length of the resilient members to provide a particular resistance force based on the resistance level indicators. For example, as shown in FIG. 1, cord locks 126 are provided at a first end of each of the resilient members 130A, 130B, 132A, 132B. Each of the cord locks 126 may be configured to slideably engage one of the resilient members 130A, 130B, 132A, 132B to adjust the resistance force that is provided by a corresponding one of the resilient members 130A, 130B, 132A, 132B. For example and referring to FIGS. 2A-2E, an exemplary cord lock for adjusting a resistance force of a resilient member in accordance with the present disclosure is shown. As shown in FIG. 2A, a cord lock may include a housing 210 having a hole 212 that extends through the housing along a first direction. The cord lock may also include a plunger 220 (e.g., FIGS. 2B-2E) having a hole 222 (e.g., FIGS. 2B-2C) that extends through a body of the plunger 220. The plunger 220 may be configured to reside at least partially within the housing 210 (e.g., FIGS. 2B-2C).

A biasing mechanism 224 may be provided to bias the plunger 220 in a first position (e.g., FIG. 2C) and pressure may be applied to the plunger 220 to bias the plunger 220 in a second position (e.g., FIG. 2B). The biasing mechanism 224 may be a spring or another type of resilient member that may be configured to bias the plunger 220 to the first position described above. When in the second position, the hole 212 of the housing 210 (e.g., FIG. 2A) and the hole 222 of the plunger 220 (e.g., labeled in FIG. 2C) may be substantially aligned (e.g., FIG. 2B), which allows a resilient member 202 (e.g., one of the resilient members 130A, 130B, 132A, 32B of FIG. 1) to be passed through the holes 212, 222. When the pressure is released, the biasing mechanism 224 may bias the plunger 224 to the first position, which causes the holes 212, 222 to become misaligned and creates a compressive force on the resilient member 202, as shown in FIG. 2C. This compressive force may hold the cord lock at a particular location with respect to the resilient member 202. For example, as shown in FIGS. 2D and 2E, the cord lock may be slid to different locations along the length of the resilient member 202 (e.g., when the pressure is applied to the plunger 220 and the holes 212, 222 are substantially aligned) and then released to lock the cord lock at a desired location along the length of the resilient member 202. As briefly described above, the resilient member 202 may include one or more resistance level indicators, such as resistance level indicators 230, 232, 234 of FIGS. 2D, 2E. Depending on which resistance level indicator is used to configure the location of the cord lock along the length of the resilient member 202, different resistance forces may be provided, thereby allowing the resistance force provided by the resilient member to be adjusted to a particular user's needs or goals. It is noted that the exemplary cord lock illustrated in FIGS. 2A-2E has been provided for purposes of illustration, rather than by way of limitation and that other types of locking mechanisms may also be utilized in accordance with embodiments of the present disclosure. Further, it is noted that the particular location along the length of a particular resilient member where the cord lock is secured may be used to provide fine tuning of the resistance force and that other mechanisms, such as the thickness of the resilient member, may also contribute to the resistance force, as described above. Thus, a resistance level indicator for a resilient member having a first thickness may provide a different resistance force than a similarly positioned resistance level indicator on a thicker or thinner resilient member.

Referring back to FIG. 1, the wearable article 100 may be recommended by a medical professional as an aid or training device to facilitate various types of treatment for patients suffering from different ailments, such as the aforementioned proprioceptive dysfunction or vestibular disorders. As part of the prescribing of the use of the wearable article 100, the medical professional may identify particular locations where resilient members should be provided, such as at the sideseam 112B of the first limb portion 112 and the inseam 124A of the second limb portion 114. Additionally, the medical professional may specify particular resistance forces that should be provided by the one or more of the resilient members. As explained above, the resilient members may be dynamically configurable to provide different resistance forces, such as by adjusting the thickness of the resilient member(s) and/or adjusting the length of the resilient member using the cord lock 126. Based on the information provided by the medical professional or physician, appropriately sized resilient members may be applied or secured to a wearable article suited for the patient.

To illustrate, a resilient member may include a first resistance level indicator that identifies a location for aligning the cord lock 126 along the resilient member to provide a first resistance force and a second resistance level indicator that identifies a location for aligning the cord lock 126 along the resilient member to provide a second resistance force. If the medical professional identified the first resistance force, the user would slide the cord lock to the position identified by the first resistance level indicator and lock the cord lock into the appropriate location, as described above with reference to FIGS. 2D, 2E, and if the medical professional identified the second resistance force, the user would slide the cord lock to the position identified by the second resistance level indicator and lock the cord lock into the appropriate location. This process may be repeated as necessary until all resilient members have been configured to the appropriate settings specified by the medical professional. It is noted that the resistance forces provided by the resilient members may be low levels of resistance force, as opposed to performing weight training, which may be inappropriate for persons suffering from proprioceptive dysfunction or vestibular disorders. As described elsewhere herein, the resistance levels will vary based on subject size, physician treatment plan, the desired measurement levels, and other factors.

Once the wearable article 100 is configured to provide the appropriate resistance forces via the specific resilient members and configurations specified by a medical professional, the user may wear the wearable article and perform one or more activities. The one or more activities may be designated by the medical professional, such as activities determined to provide the resistance forces to specific muscle groups. Additionally or alternatively, the user may engage in normal day to day activities and the resistance forces generated by the resilient members as the user performs those activities may train the user's muscles to provide appropriate reactions to those forces, such that over time the user's body learns to trigger the appropriate muscle responses as the user performs those activities. It is noted that although a user may begin treatment with the wearable article 100 having a first configuration, the particular configuration of the wearable article may change over time, such as to decrease the resistance forces or to utilize different resistance forces to train other aspects of the user's body, proprioceptive senses, or for other purposes.

As briefly described above, the cord locks 126 may be utilized to adjust the resistance forces provided by the resilient members. In an aspect, the particular locations where the resistance level indicators are provided may be determined based on characteristics of the target user. For example, as the length of the resilient member(s) changes, the resistance force may also change. Due to physical differences between different users, such as different leg lengths between a first user and a second user, the particular locations of the resistance level indicators may also be different. Stated another way, a resistance level indicator associated with a first resistance force may be provided at a first location of the resilient member or a second location of the resilient member depending on the physical characteristics of the user (e.g., a tall user and a shorter user may have resilient members that provide the resistance level indicator for the first resistance level at different locations).

The particular location of the different resistance level indicators may be calculated using Young's modulus, which measures the ability of a material to withstand changes in length when under lengthwise tension or compression. For example, the particular location where a resistance level indicator should be provided may be determined according to:

$$E = \frac{F/A}{\Delta L/L}, \quad \text{(Equation 1)}$$

where E represents Young's modulus of the resilient member, F is the force, A is the area, $\Delta L$ is the change in length, and L is the length. Once the value of Young's modulus is known for the particular material used for the resilient member(s), the appropriate force for a given length may be determined, thereby allowing the resistance level indicators to be placed at appropriate locations. By utilizing precise measurements, the wearable articles of embodiments may be configured to provide precise resistance forces customized to the needs of each unique and individual user. Additionally, utilizing Equation 1, appropriate and precise measurements for configuring the resistance level indicators may be determined for different sized resilient members (e.g., resilient members having different thicknesses, etc.). This enables a greater range of resistance forces and applications for which the wearable article may be utilized to treat various ailments.

In an embodiment, resilient members may be provided with limiters 150 configured to prevent the resilient member(s) from being configured to an improper or excessive resistance force. The limiters 150 may be configured to prohibit the cord locks from sliding past the limiters 150. In an embodiment, the limiters 150 may simply be knots tied in the resilient members. In another embodiment, the limiters 150 may be another type of device that is clamped onto or otherwise attached to the resilient members at a desired location to prevent improper configuration of the resistance forces provided by the resilient members.

As shown above, the wearable article 100 provides an improved technique for treating certain physical ailments, such as proprioceptive dysfunction and vestibular disorders. Further, the wearable article 100 enables dynamic configuration of the resistance forces provided by the resilient members and may be easily performed by a user or the user's parent (e.g., if the user is a child). The resistance forces provided by the resilient members of the wearable article 100 may train the user's body to provide appropriate proprioceptive responses to certain activities, which may enable the user to enjoy a better quality of life, become more self-confident, and overcome other challenges caused by such ailments. Additionally, researchers have found a correlation between improved motor development with improvements in cognitive abilities due to spectral awareness and increased independence which is correlated with maturity and greater cognition. Such benefits may be realized by patients that are treated with wearable articles configured in accordance with embodiments of the present disclosure.

Referring to FIG. 3, an embodiment of a system for monitoring treatment of a patient via a wearable article according to aspects of the present disclosure is shown as a system 300. As shown in FIG. 3, the system 300 may include a wearable article, such as the wearable article 100 of FIG. 1, and a remote device 310. The wearable article illustrated in FIG. 3 includes the features described above with reference to FIG. 1, and also includes one or more strain gauges. For example, in FIG. 3, strain gauges 302A, 302B, 304A, 304B are shown. The strain gauges may be configured to detect the resistance forces provided by each of the resilient members configured for the wearable article. In particular, strain gauge 302A may be configured to measure the resistance force provided by resilient member 130A, strain gauge 302B may be configured to measure the resistance force provided by resilient member 130B, strain gauge 304A may be configured to measure the resistance force provided by resilient member 132A, and strain gauge 304B may be configured to measure the resistance force provided by resilient member 132B.

The strain gauges 302A, 302B, 304A, 304B may be communicatively coupled to a communication interface 306 via communication links 312. As the strain gauges detect resistance forces information representative of the resistance forces may be provided to the communication interface 306 via the communication links 312 and the communication interface 306 may be configured to transmit the information associated with the resistance force measurements to the remote device 306. In an aspect, the communication interface 306 may include a Bluetooth communication interface configured to communicate with the remote device 310 via a wireless communication link (e.g., a Bluetooth communication link). In other aspects, the communication interface 306 may configured to communicatively couple to the remote device 310 via another type of communication link established according to another network communication protocol (e.g., a cellular communication link, a Wi-Fi communication link, ANT+, etc.).

In an aspect, the communication interface 306 may be disposed proximate the back yoke portion 148 illustrated in FIG. 1. Positioning the communication interface 306 in this manner may provide more comfort to the user during use of the wearable article. It is noted that positioning the communication interface 306 at the back yoke portion 148 has been provided for purposes of illustration, rather than by way of limitation and that the communication interface 306 may be located elsewhere on the wearable article, such as near or within a pocket (if present), depending on the particular configuration of the wearable article as well as the type of wearable article (e.g., a shirt, pants, etc.).

As shown in FIG. 3, the remote device 310 may include a one or more processors 312, a memory 314, one or more communication interfaces 320, and one or more input/output (I/O) devices 322. The memory 314 may store instructions 316 that, when executed by the one or more processors 312, cause the one or more processors 312 to perform the operations described in connection with monitoring use of a wearable article via the remote device 310 in accordance with the present disclosure. Additionally, the memory 314 may store one or more databases 318, described in more detail below. The one or more communication interfaces 320 may be configured to communicatively couple the remote device to one or more communication networks (e.g., a Wi-Fi network, a cellular communication network, etc.) as well as communicatively couple the remote device 310 to the communication interface 306, as described above. The I/O devices 322 may include a display device (e.g., a touchscreen display or other type of display device), a keyboard, a microphone, a speaker, a mouse, or other devices facilitating user interaction with the remote device 310 to facilitate the operations described herein. The one or more databases 318 may store records associated with resistance force measurements received from the communication interface 310 over time. These records may enable the progress of the user's treatment using the wearable article to be tracked over time and potential modifications to be made (e.g., to the resistance forces) where appropriate.

In an embodiment, the remote device 310 may be a device associated with a user, such as a cell phone or smartphone of the user (or the user's parent(s) if the user is a child). The instructions 316 may include instructions providing a monitoring application that enables the user to monitor the resistance forces experienced during use of the wearable article. For example, the application may be configured to receive the information associated with the resistance forces from the communication interface 310 and present the information at the display device of the remote device 310. The information may be presented via a graphical user interface. In an aspect, the graphical user interface may be provided via a web-based application accessible via a webbrowser application of the remote device 310. Alternatively, the graphical user interface may be provided by a standalone application executing on the remote device, such as an application downloaded and installed to the remote device (e.g., a smartphone device, a tablet computing device, and the like) from an appstore or an application executing on a desktop or laptop computing device. The application may be configured to track the resistance forces experienced by the user over time. Tracking the resistance forces may include presenting various types of information to the user associated with resistance forces experienced by the user. This may enable the user to verify that the regimen of training/rehabilitation recommended by a medical professional is being followed and may increase the rate at which the user realizes the benefits (e.g., physical benefits, emotional benefits, and the like) facilitated by the user of wearable articles in accordance with the present disclosure. It is noted that the monitoring functionality may also be facilitated and/or supported via a cloud-based system. For example, the web-based application and/or the standalone application may provide the user interface through which a user (e.g, a patient being treated by a wearable article, a physician, a guardian of the patient, etc.) accesses and communicates or exchanges information with the cloud-based system. The cloud-based system may include one or more databases where information generated during treatment of a patient may be stored (e.g., for access and review by a physician to verify the treatment being provided is appropriate, etc.). It is noted that other functionality for supporting monitoring of a treatment plan of a user described herein may also be performed, entirely or in part, by the cloud-based system.

The remote device may also be configured to receive information that identifies a predetermined amount of resistance force. The predetermined amount of resistance force may correspond to the resistance force recommended by a medical professional. Such information may be input by the user or may be automatically received from the medical professional (e.g., the medical professional may also have a remote device 310 having the application and the information input by the medical professional may be propagated to the account of the user). The application (and/or the cloud-based system) may be configured to determine whether one or more of the cord locks are slideably engaged with the one or more resilient members at a correct location based on the information representative of the resistance forces received from the communication interface 310. For example, the application may determine whether the resistance force associated with a first resilient member matches a predetermined amount of resistance force (e.g., the recommended resistance force indicated by the medical professional) to within a threshold tolerance (e.g., a threshold percentage, amount of force, etc.). The application may generate an alert when the resistance force does not match the predetermined amount of resistance force to within the threshold tolerance. For example, if the measured resistance force exceeds the predetermined resistance force by a particular amount, the application may determine that the measured resistance force does not match the predetermined resistance force to within the threshold tolerance and may generate the alert. Similarly, if the if the measured resistance force is below the predetermined resistance force by a particular amount, the application may determine that the measured resistance force does not match the predetermined resistance force to within the threshold tolerance and may generate the alert. The alert may notify the user that at least one of the resilient members of the wearable article is configured improperly and may prompt the user with instructions to correct the configuration of the resilient member, such as indicating the particular resistance level visual indicator that should be used to configured the resistance force of the resilient member or providing other information that enables the user to correct the configuration of the wearable article. If the measured resistance force matches the predetermined resistance force to within the threshold tolerance, the application may present one or more graphical indicators at the graphical user interface to indicate that the wearable article is properly configured.

An additional advantage of the communication interface 306 of the wearable article is that the resistance force measurements may also be provided to the medical professional, thereby enabling the medical professional to remotely monitor the user's use of the wearable article and ensure that the treatment schedule is followed. For example, if no measurements are received for a period of time, the medical professional may be notified via an alert notification, which may prompt the medical professional to contact the user to inquire about the lack of measurements and ensure that the user is treated appropriately.

Additional exemplary functionality that may be provided to manage treatment of a patient may also be provided. For example, the application and/or cloud-based system may be configured to track a length of time that the wearable article was used, such as to note a time period during which measurements were received (e.g., during treatment of a patient). The wearable article may be configured initiate tracking the duration of a treatment session upon detecting that the resilient members are generating forces (e.g., by detecting the force via feedback provided by the strain gauge(s)). In an aspect, upon detecting forces are being generated, the communication interface 306 may automatically begin transmitting force measurements to the remote device(s) 310. Alternatively or additionally, the wearable article may include an on/off switch and measurements may begin being transmitted upon turning on the wearable article and may stop when turned off. In an aspect, the measurements may be transmitted from the remote device to a database (e.g., a database supported by the cloud-based system) with information that identifies the particular user corresponding to the measurements, such as by including an identifier with the measurements. The measurements may be timestamped and the timestamps may be used to determine when a treatment session begins and ends. Based on the start and end times for the treatment session, the total duration of the treatment session may be determined, which may enable a physician to verify that the user is following the correct treatment plan.

The remote device 310 may also be configured to provide feedback to the patient. For example, the user interface presented at the remote device (e.g., a mobile device or computing device associated with the patient or other person overseeing the patient's treatment) may provide one or more measurement indicators. The measurement indicators may indicate the appropriate configuration of the cord lock(s) with respect to the resistance level visual indicators, which enables the patient to verify the wearable article is appropriately configured for the treatment session. In addition to indicating the correct configuration of the resilient members, the feedback presented at the interface may indicate minimum and maximum resistance levels to be used during the treatment session. Additionally, the information presented to the user may provide optimal zone indicators. In an aspect, the parameters used for treatment (e.g., the level of resistance force provided, the duration of a treatment session, the location of the resilient members, and the like) may be changed over time, such as after the patient has made improvements with respect to the condition being treated or for some other reason. When the medical professional determines the treatment parameters should be modified, the medical professional may update the treatment plan for the patient and transmit a notification to the patient's electronic device that indicates the new treatment parameters.

The cloud-based system supporting the application may be configured to monitor received information and generate various alarms and notifications based on the received information. Alarms can be configured to notify the patient and/or physician when the patient has exceeded a scheduled amount of treatment time (e.g., to prevent overtreatment). To illustrate, suppose the patient is to receive 4 hours of treatment during a weak. If the system detects (e.g., based on the timestamps of the received resistance force measurements) that the user has performed more than 4 hours of treatment, an alarm may be generated to signal that the patient should stop treatment until a certain amount of time has elapsed (e.g., a beginning of a new cycle of the treatment plan). Alarms may also be generated if the received resistance force measurements indicate that the patient is being treated with a resistance force that exceeds a maximum resistance force appropriate for the patient's treatment plan, which may be an indication that the wearable article is not properly configured or that a malfunction has occurred. This type of alarm may prevent the patient from incurring an injury or other harmful result due to overtraining or improper training. In addition to the functionalities described above, the patient and/or medical professional may be presented with information that indicates the total weight resisted or lifted based on the power output information provided by the strain gauge(s) and total watts output. The information presented to the patient and/or medical professional may also indicate the measure of resistance between right and left sides (or other relative measurements) and indications regarding body symmetry.

In an aspect, data may be compiled as a result of treatment and monitoring of a large number of patients over a time period, which may provide a litany of collected information regarding treatment of various conditions using wearable articles configured according to embodiments of the present disclosure. From this compiled data statistical analysis may be performed and trends may be identified, such as identification of treatment plans that successfully treated patient conditions, time frames for treatment, movements or exercises that promoted desired results, resistance force levels utilized to successfully treat patients, or other indications of treatment plan successes and effectiveness. The data may also be utilized to map nerve group deterioration across a muscle group or body region, which may improve the medical community's understanding of how certain conditions treated using wearable articles of the present disclosure impact the human body. This data may be shared with the medical community to further help address trends and improve the efficacy of treatment types and any number of nuances in the overall medical treatments for which wearable articles configured in accordance with the present disclosure may be applied.

As described above with reference to FIGS. 1-3, the wearable articles, systems, and methods of the present disclosure provide new techniques for treating certain ailments, such as ailments caused by proprioceptive dysfunction or vestibular disorders. Embodiments enable resistance training to be performed using small amounts of resistance to muscle groups targeted based on the specific symptoms of the user. Additionally, features of the present disclosure simplify the configuration of the wearable article to provide appropriate levels of resistance force through the use of limiters, cord locks, and resistance level indicators that allow precise tuning of the resistance force applied by each resilient member. Automatic and remote monitoring may also be provided by incorporating electronic strain gauges and a communication interface into the wearable article. This provides an automated way to verify the wearable article is properly configured as well as monitor the user of the wearable article (e.g., to ensure that a treatment plan is being followed and determine whether adjustments to the treatment plan are appropriate).

In addition to the benefits and improvements described above, embodiments may provide other advantages to the user. For example, the present invention may be highly beneficial to specific groups of children and other persons that suffer emotional stress due to proprioceptive dysfunction vestibular disorders. Parents working with their children to complete the prescribed regimen of exercises also strengthen the parent-child bond, thereby improving the emotional development of the child in addition to the physical improvements the child will realize. Additionally, treatments utilizing the wearable articles and systems disclosed herein may also increase the safety to the user, who may not be able to lift certain amounts of weight due to the ailments they suffer, especially for small children. As shown above, treatment of certain conditions such as proprioceptive dysfunction and vestibular disorders using embodiments of the present disclosure may allow a user to fundamentally retrain the user's base line of the body's position and the sense of movement and overcome many of the negative impacts that such conditions have on the user.

Figure 5:
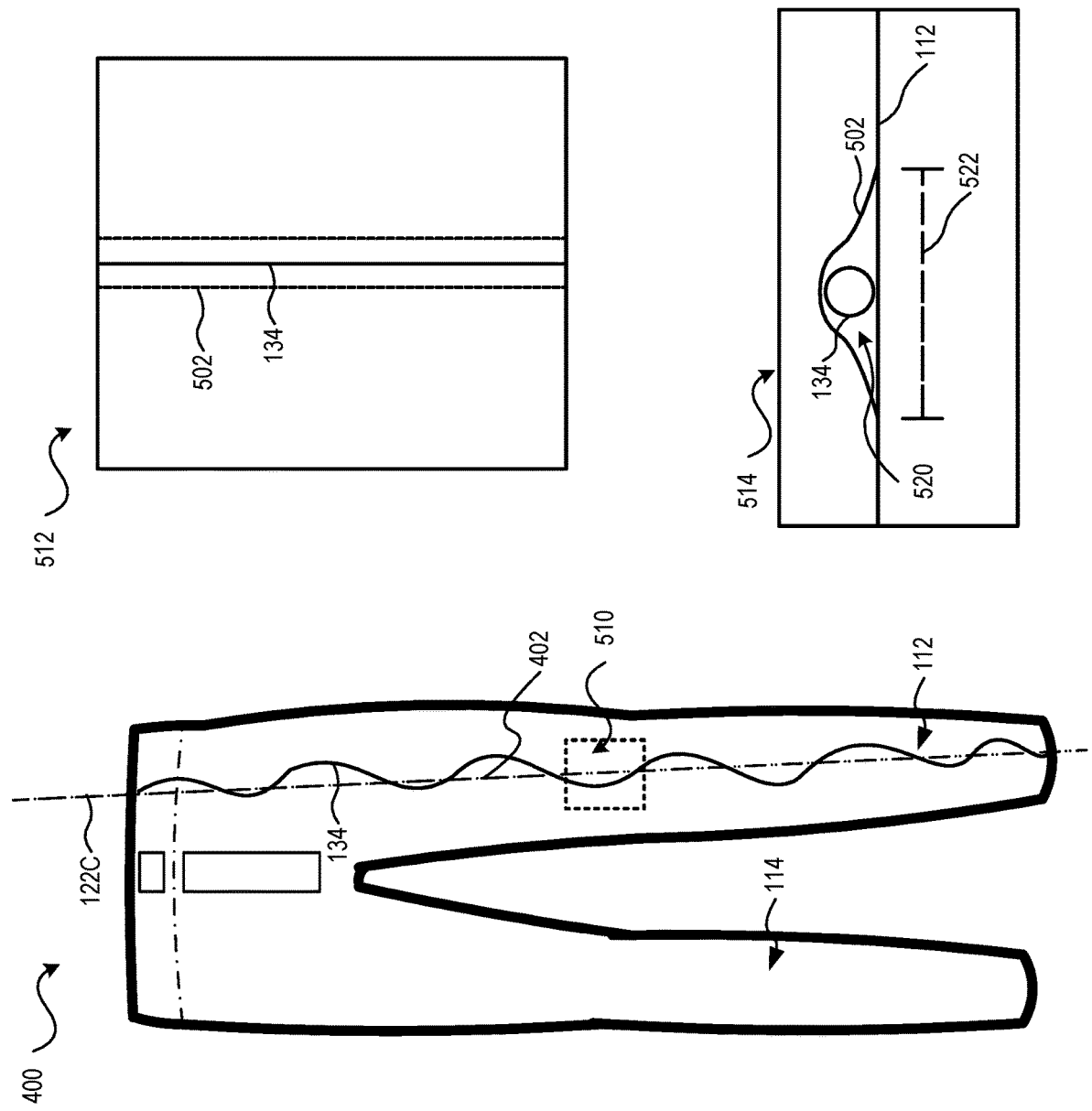
FIG. 5 is a block diagram illustrating a resilient member channel configured in accordance with aspects of the present disclosure.

Referring to FIG. 5, a block diagram illustrating a resilient member channel configured in accordance with aspects of the present disclosure is shown. As described above with reference to FIGS. 1, 3, and 4, wearable articles configured in accordance with embodiments may include one or more resilient members configured to provide a resistance force to a patient. In FIG. 5, the resilient member 134 of FIG. 4 is shown disposed along the length of the front (e.g., 122C) of the limb portion 112 of the wearable article 400. Additionally, a callout 510 is shown. A zoomed in view 512 of callout 510 is shown to the right. If a patient wearing the wearable article 400 would bend at the knee, the resilient member 134 may slide to the side of the knee, which may prevent the resilient member form 134 from providing the appropriate resistance force (e.g., because the sliding movement may prevent the resilient member 134 from stretching to a desired length).

To mitigate such instances, a wearable article configured in accordance with aspects of the present disclosure may include a resilient member channel, such as resilient member channel 502 shown in zoomed in view 512. The resilient member channel 502 may be configured to restrict movement of the resilient member 402, such as to prevent the above-described sliding of the resilient member 134, which may prevent the resilient member 134 from providing an appropriate resistance forces. As shown in profile view 514, the resilient member channel 502 may be formed as a strip of material that is placed over the resilient member 134. The peripheral edges of the resilient member channel 502 may be attached to a surface of the wearable article 400 along a desired path (e.g., 122C) of the resilient member 134. For example, material of the resilient member channel 502 may be sewn in place, glued in place, or held in place by some other mechanism (e.g., Velcro, snap fasteners, buttons, etc.).

A space 520 may be defined between the material used to form the resilient member channel 502 and the surface of the wearable article 400 (e.g., the surface of the limb portion 112) forming a channel that the resilient member 134 may pass through. A smaller space 520 may provide greater restriction of lateral or undesired movement by the resilient member 134 and increase the likelihood that the correct resistance force is applied during treatment of the patient. For example, a distance 522 between the edges of the material used to form the resilient member channel 502 may be used to control the size of the space 520 and control the amount of lateral movement that the resilient member 134 has. For example, a smaller distance 522 may decrease the size of the space 520 and the amount of lateral movement that the resilient member 134 has and a larger distance 522 may increase the size of the space 520 and the amount of lateral movement that the resilient member 134 has. It is noted that resilient member channels, such as the resilient member channel 502, are not limited to straight line orientations. For example, a resilient member channel may include a portion that is vertically oriented (e.g., along length 122C), a portion that is oriented at an angle with respect to the vertically oriented portion, or even have a curved orientation. Further, it should be understood that the resilient member channels may have uniform distances 522 over their entirety or may have non-uniform distances 522 (e.g., a first portion of a resilient member channel may have a first distance providing a first freedom of movement for the resilient member and a second portion of the resilient member channel may have a second distance that is different from the first distance and provides a greater or lesser freedom of movement for the resilient member).

Figure 6:
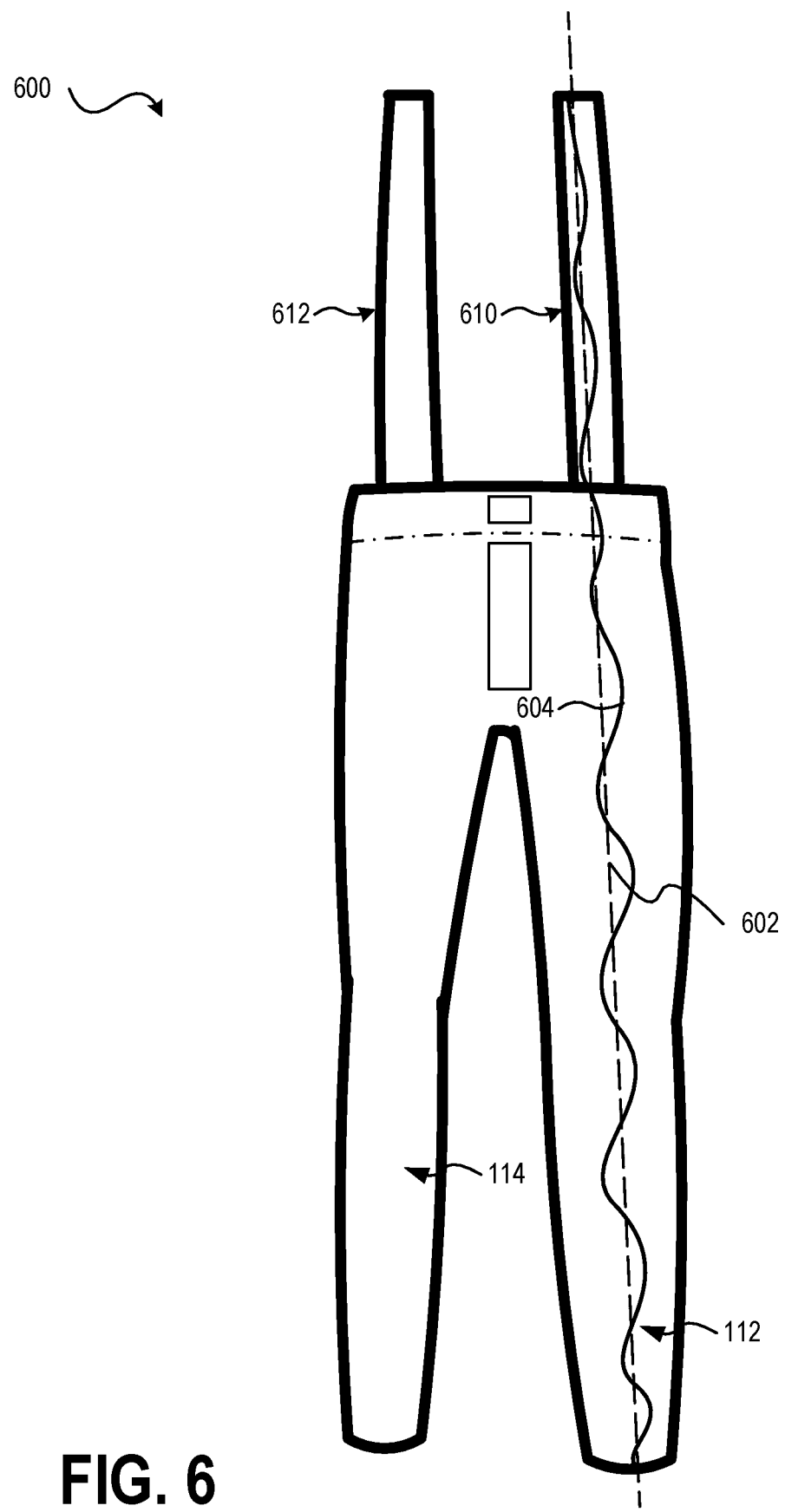
FIG. 6 is a block diagram illustrating additional aspects of a wearable article in accordance with the present disclosure.

Referring to FIG. 6, a block diagram illustrating additional aspects of a wearable article in accordance with the present disclosure is shown as a wearable article 600. In FIG. 6, the wearable article 600 includes a shoulder harness or assembly. In the particular example shown in FIG. 6, the should harness or assembly includes shoulder straps 610, 612 and a resilient member 604 is disposed along path 602. The resilient member 604 may be anchored at the bottom of limb portion 112 and proximate the top of shoulder strap 610. The shoulder harness or assembly may be utilized in situations where higher resistance forces are provided by the resilient members and to maintain a resting length of the resilient members. The resilient member 604 may be situated within a resilient member channel, such as the resilient member channels described above with reference to FIG. 5, that is disposed on an external or internal surface of the shoulder strap 610. It is noted that the resilient member 604 may be anchored at the top of the shoulder strap 610 or may be anchored at another position, such as a midpoint of the should strap 610 or even on a back side of the should strap 610 (front side shown in FIG. 6). It is further noted that shoulder harnesses or assemblies are not limited to just shoulder straps. For example, a should harness or assembly may include material disposed between the shoulder straps 610, 612, which may increase the amount of support provided by the shoulder harness or assembly, provide additional areas where control of the path a resilient member may be provided, or may simply be provided for aesthetic purposes. Additional exemplary aspects for configuring resilient members in connection with shoulder harnesses or assemblies are illustrated and described below with reference to FIGS. 7 and 8.

Figure 7:
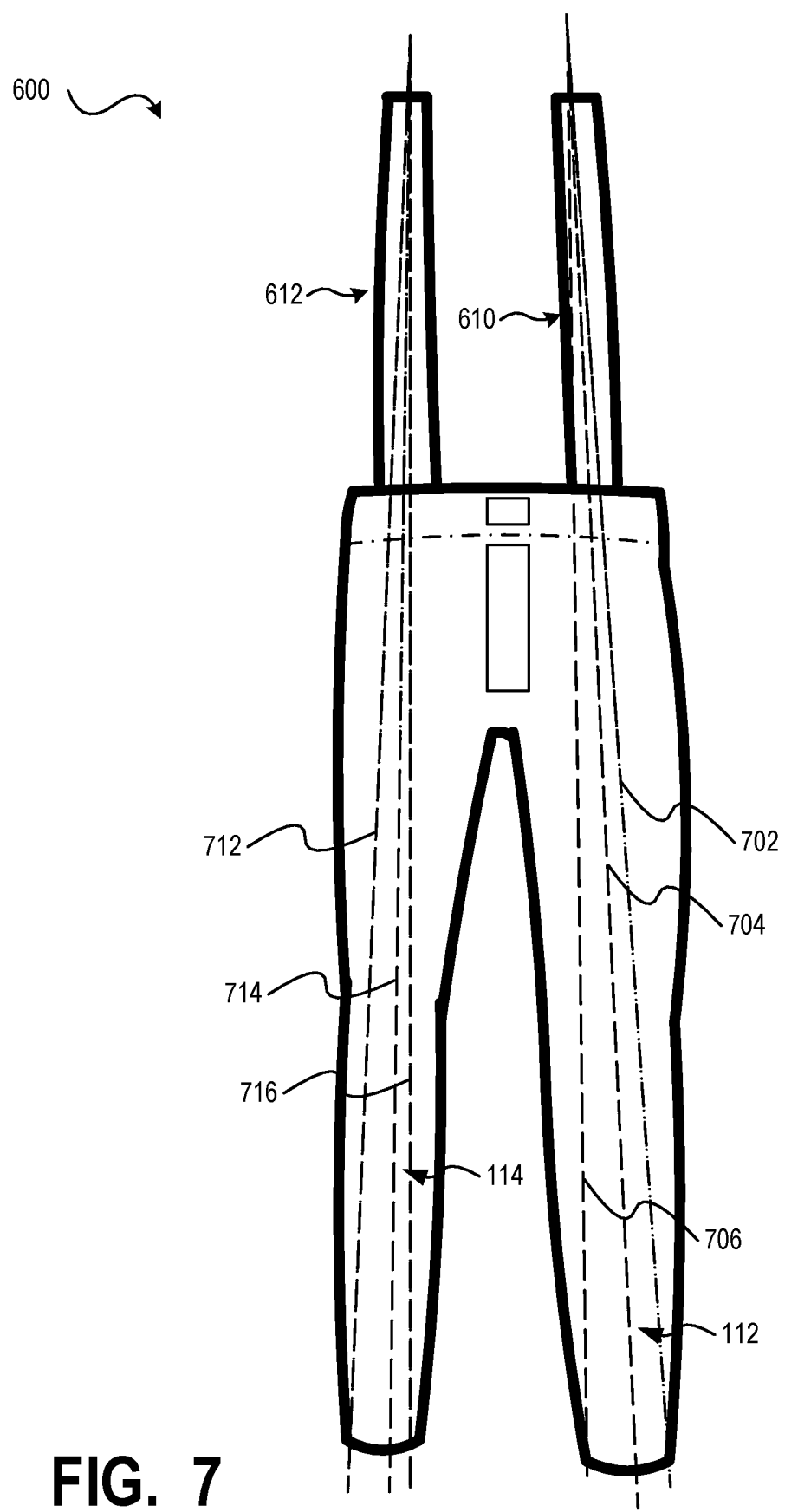
FIG. 7 is a block diagram illustrating aspects of utilizing shoulder straps with a wearable article configured according to the present disclosure.
Figure 8:
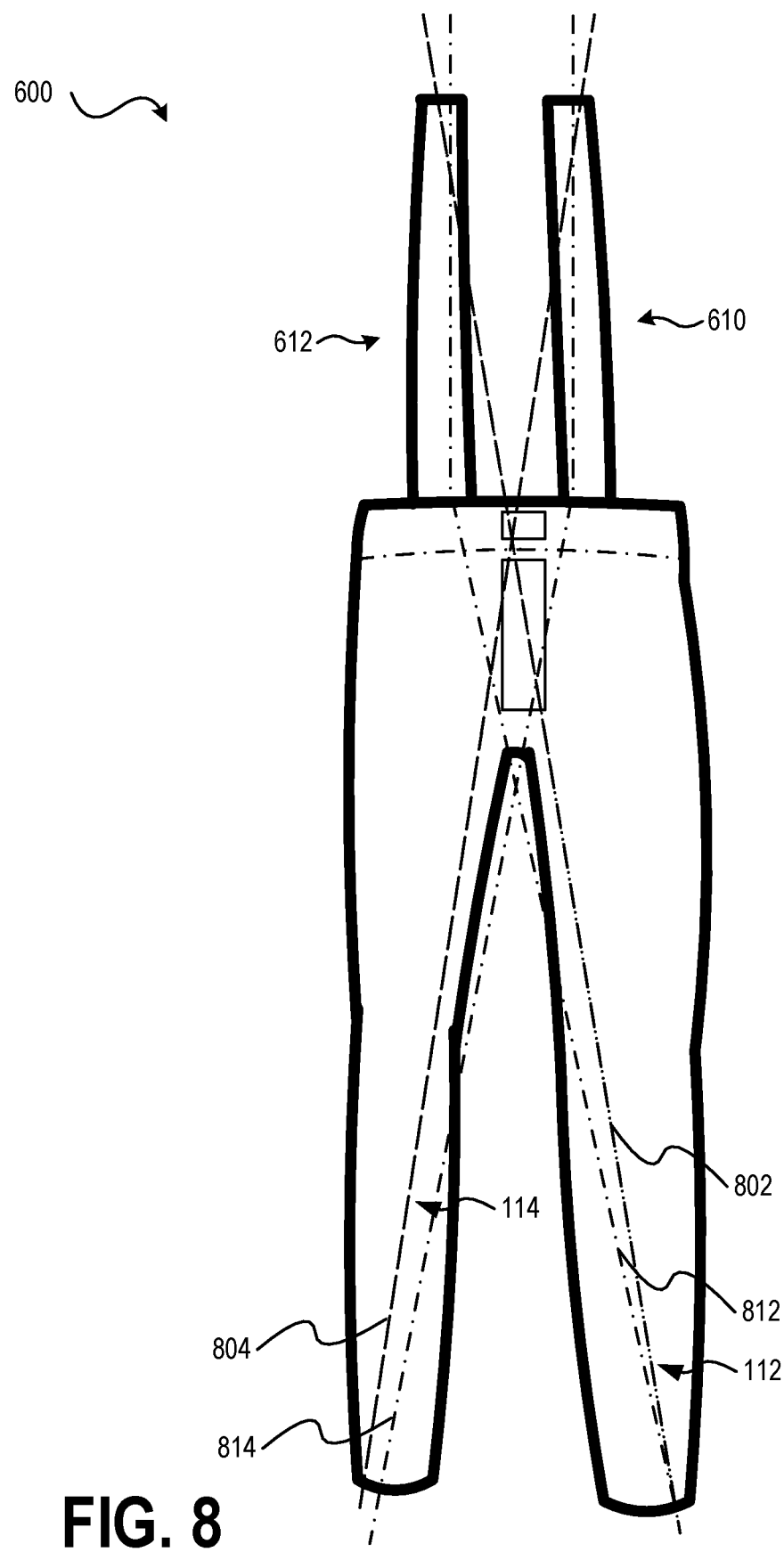
FIG. 8 is a block diagram illustrating additional aspects of utilizing shoulder straps with a wearable article configured according to the present disclosure.

Referring to FIGS. 7 and 8, block diagrams illustrating aspects of utilizing shoulder harnesses or assemblies with a wearable article configured according to the present disclosure are shown. In FIGS. 7 and 8, lines 702, 704, 706, 712, 714, 716, 802, and 804 represent exemplary paths along which resilient members may be provided for various configurations of wearable articles utilizing shoulder harnesses or assemblies in accordance with aspects of the present disclosure. As shown in FIG. 7, resilient members may be disposed along paths 702, 712 running from an upper portion of shoulder straps 610, 612 to an outer edge of the leg portions 112, 114 proximate the patient's ankle, paths 704, 714 running from an upper portion of shoulder straps 610, 612 to a midpoint of the leg portions 112, 114 proximate the patient's ankle, paths 706, 716 running from an upper portion of shoulder straps 610, 612 to an interior edge of the leg portions 112, 114 proximate the patient's ankle, and paths 802, 804 running from an upper portion of shoulder straps 610, 612 to a base of the leg portions 112, 114, where path 802 crosses from the right side of the patient to the left side of the patient and path 804 crosses from the left side of the patient to the right side of the patient (assuming the patient would be facing the reader when viewing FIGS. 7 and 8). Additionally, FIG. 8 illustrates resilient member paths 812, 814, which extend vertically along the length of shoulder straps 610, 612 and then cross over to the bottom edge of limb portions 112, 114. It is noted that the exemplary resilient member paths illustrated in FIGS. 7 and 8 are intended for purposes of illustrating ways in which resilient members may be configured for applications where a shoulder harness or assembly is utilized, however, such illustration is intended to demonstrate the paths of the resilient members conceptually rather than literally and thus the paths illustrated in the drawings may be slightly different from those that may be provided to a particular patient. For example, the height and width of each patient may vary, which may introduce some variation in the particular paths utilized for one or more resilient members. Further, some of the paths illustrated in FIGS. 7 and 8 include portions that may appear external to the wearable article and/or shoulder harness or assembly, but in reality such paths may be limited to the contours and available space on the interior and/or exterior surfaces of the wearable article and shoulder harness or assembly.

Figure 9:
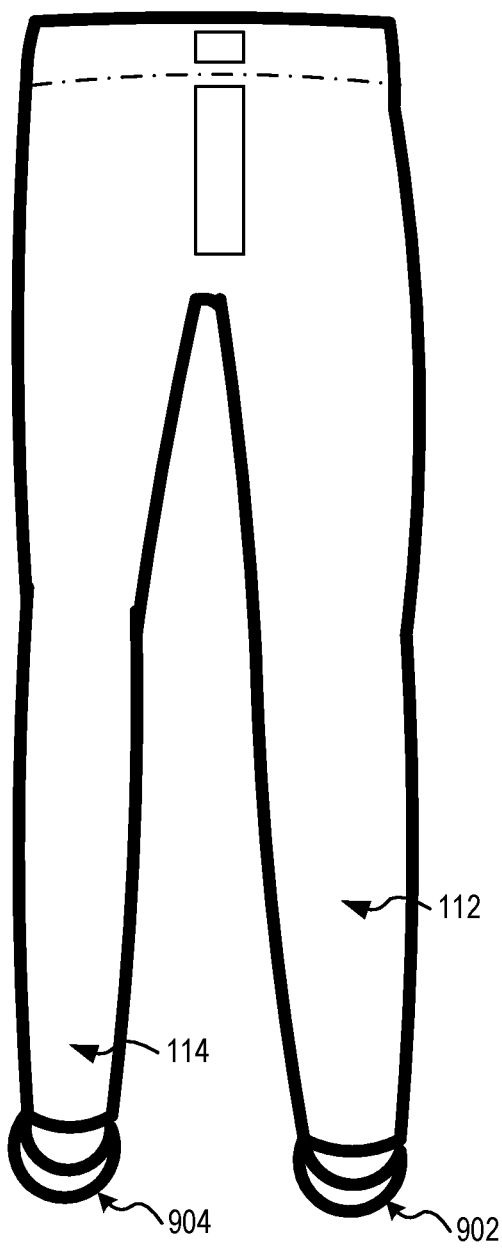
FIG. 9 is a block diagram illustrating aspects of utilizing ankle straps with a wearable article in accordance with the present disclosure.

Referring to FIG. 9, a block diagram illustrating an additional aspect of a wearable article in accordance with the present disclosure is shown. For some applications of wearable articles configured in accordance with the present disclosure, one or more ankle straps 902, 904 may be provided. The ankle straps, when provided, may be attached to the bottom edge of the limb portions 112, 114 of the wearable article. The ankle straps 902, 904 may improve the overall performance of the wearable articles by ensuring that the resistance forces are consistent during treatment of the patient. For example, if the limb portions 112, 114 are not maintained snugly against the patient's limbs (e.g., legs) during the providing of the resistance forces, the limb portions 112, 114 may deform under the resistance force and slide up, which would result in an incorrect resistance force being provided by the resilient members. By providing the ankle straps 902, 904 the resistance forces may be maintained at a constant level because the ankle straps 902, 904 may prevent the limb portions 112, 114 from deforming or rising up as the resistance forces are provided. The ankle straps 902, 904 may be secured to the limb portions 112, 114 in various ways. For example, the ankle straps 902, 904 may be sewed onto the lower edge of the limb portions 112, 114, secured using Velcro, or some other type of technique may be used to secure the ankle straps 902, 904 to the limb portions 112, 114. In an aspect, a metal grommet may be provided proximate the location where the ankle straps 902, 904 are secured to the limb portions 112, 114. The metal grommet may allow a resilient member to exit the resilient member channel and be exposed to an outside of the wearable article (e.g., in order to facilitate fine tuning of the resistance force using the techniques described above with reference to FIGS. 1 and 2). It is noted that in applications where resilient members are only provided for one limb portion, only one ankle strap may be provided. Alternatively, two ankle straps may be provided despite one of the ankle straps being secured to a limb portion that does not include a resilient member, such as for aesthetic purposes or for some other reason.

Figure 10:
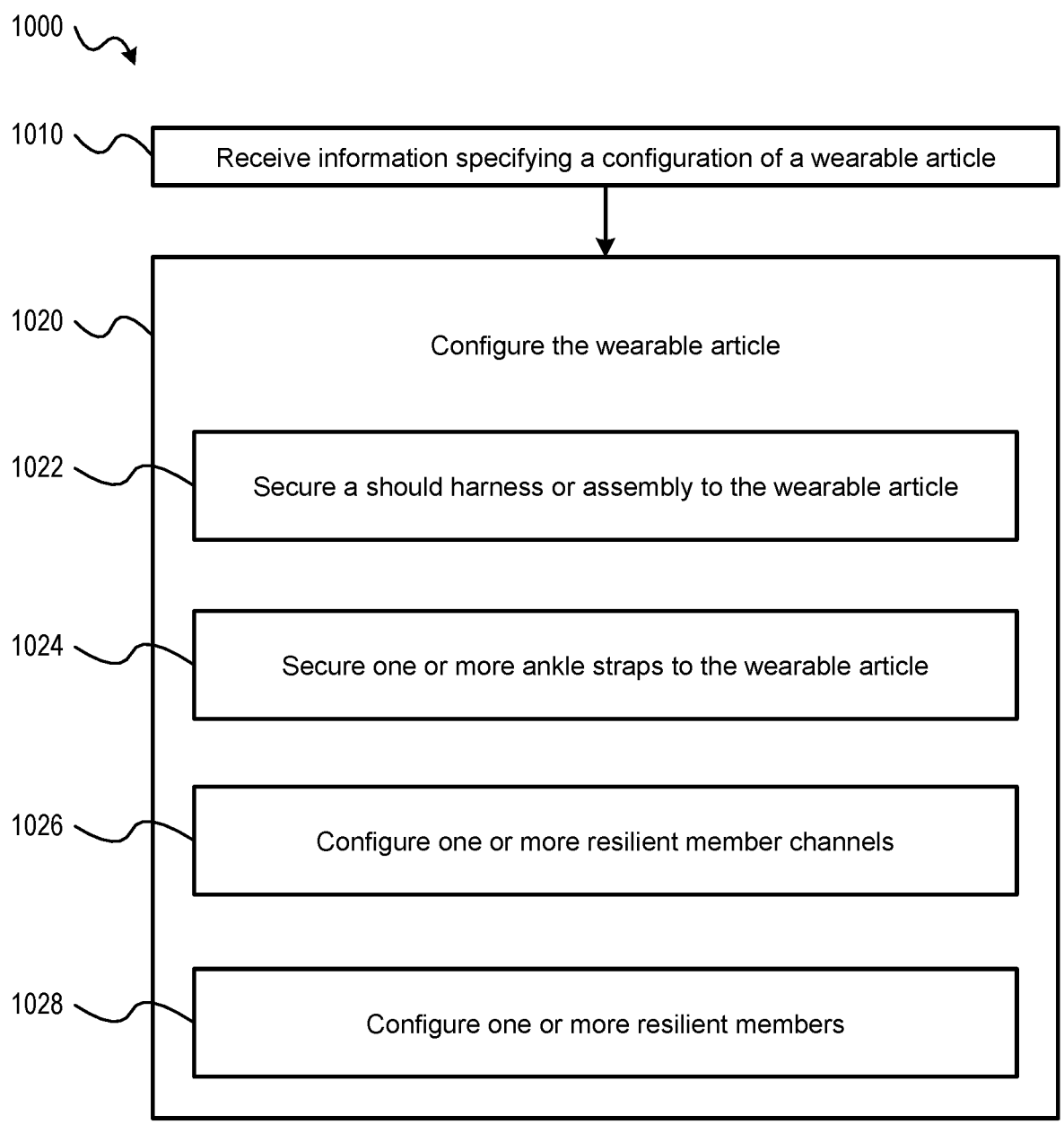
FIG. 10 is a flow diagram of an exemplary method for configuring a wearable article in accordance with aspects of the present disclosure.

Referring to FIG. 10, a flow diagram of an exemplary method for configuring a wearable article in accordance with aspects of the present disclosure is shown as a method 1000. In an aspect, the method 1000 may be used to configure a wearable article in accordance with the various aspects described above with reference to FIGS. 1-9. At step 1010, the method 1000 includes receiving information specifying a configuration of a wearable article. As described above, the configuration of the wearable article may include information indicating a number of resilient members to be provided, an orientation or path for each resilient member (e.g., inseam, sideseam, front, back, wrapping around, angular, etc.), anchor points for each end of the resilient member(s), an amount of resistance force to be provided by each resilient member, a type (e.g., pants, shirt, etc.) and size of the wearable article (e.g., inseam and waist size for pants, chest and shoulder measurements, etc.), whether a shoulder harness or assembly and/or ankle straps are to be provided, or other information (e.g., a color or other type of indicator of the material that is to be used for the wearable article, and the like).

At step 1020, the method 1000 includes configuring the wearable article. Configuring the wearable article may involve a multistep process. For example, at step 1022, a should harness or assembly may be secured to the wearable article if appropriate (e.g., if the configuration information indicates a shoulder harness or assembly should be provided). At step 1024, one or more ankle straps may be secured to the wearable article. At step 1026, resilient member channels for each resilient member may be formed on the wearable article. At 1028, one or more resilient members may be configured, which may include selecting and cutting resilient members to appropriate lengths (or the selected resilient members may be pre-cut) that provide the specified resistance forces, configuring resistance level indicators (e.g., the resistance force level indicators described with reference to FIGS. 2D and 2E), passing the resilient member(s) through the resilient member channel(s), providing cord locks at one or more ends of the resilient members and/or securing the resilient members to the wearable article (e.g., at ends not configured with cord locks).

Figure 11:
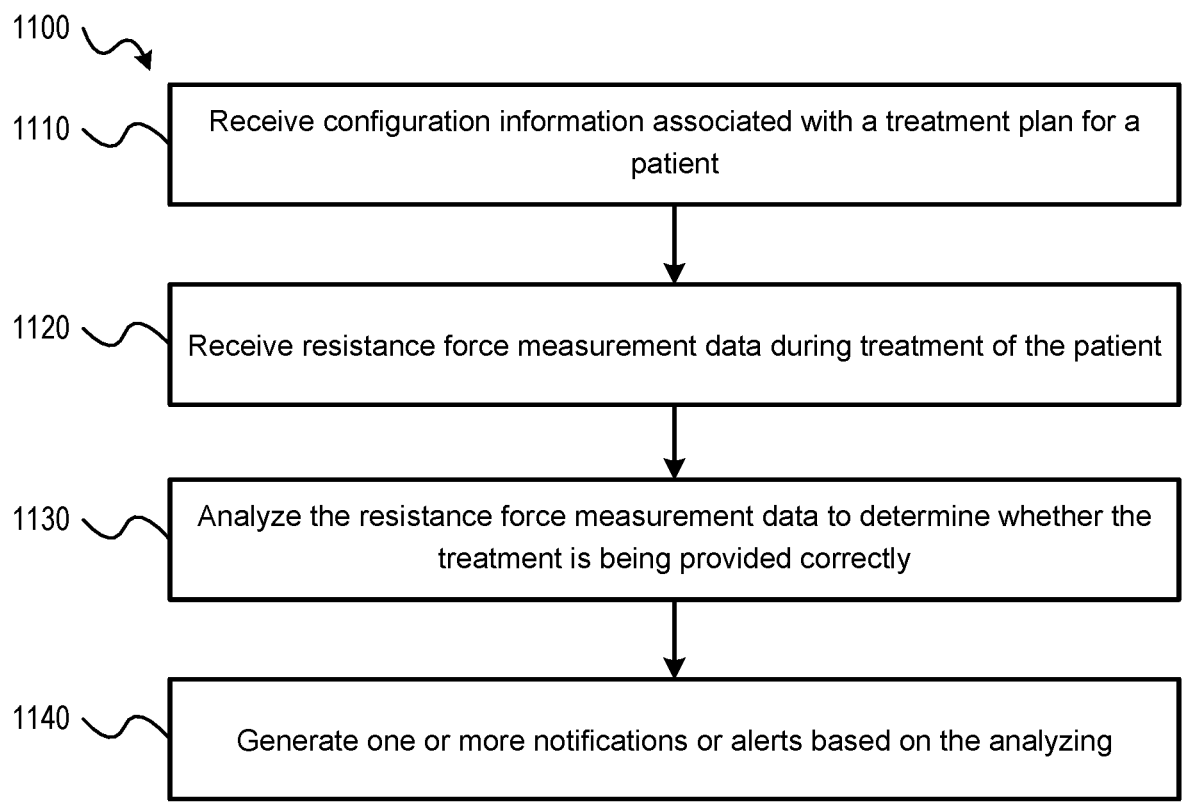
FIG. 11 is a flow diagram of an exemplary method for monitoring a patient in accordance with aspects of the present disclosure.

FIG. 11 is a flow diagram of an exemplary method for monitoring a patient in accordance with aspects of the present disclosure is shown as a method 1100. In an aspect, the steps of the method 1100 may be stored as instructions (e.g., the instructions 316 of FIG. 3) that, when executed by one or more processors (e.g., the one or more processors 312 of FIG. 3), cause the one or more processors to perform operations for monitoring a patient in accordance with aspects of the present disclosure. Additionally, it is noted that the method 1100 may facilitate the monitoring of treatment of a patient by a medical professional, the patient, or a guardian of the patient.

At step 1110, the method 1100 includes receiving configuration information associated with a treatment plan for a patient. The configuration information for the treatment plan may indicate the amount of resistance force to be provided during the treatment, a duration of treatment for a period of time (e.g., a single treatment session, an amount of time that treatment should be provided on a daily, weekly, or monthly basis), or other information associated with treatment of the patient (e.g., one or more recommended activities or motions to perform during treatment, and the like). The configuration information may be received at an electronic device associated with a medical professional or a user (e.g., the patient, patient's guardian, etc.), as described above with reference to FIG. 3. When the configuration information is received at an electronic device of the medical professional, the configuration information may be provided as inputs by personnel of the medical professional, such as a doctor, a nurse, a physical therapist, and the like. Once input to the medical professional's electronic device, the configuration information may be transmitted to a second electronic device (e.g., the electronic device associated with the patient or patient's guardian), where the information may be provided to an application accessible via the second electronic device. As described above with reference to FIG. 1-11, once the configuration information for the patient's treatment has been determined, a wearable article tailored to facilitate treatment of the patient may be provided. The wearable article may include strain gauges and a communication interface that enable resistance force measurements to be provided to a remote device, such as the electronic devices of the medical professional and/or the patient or patient's guardian.

At step 1120, the method 1100 includes receiving resistance force measurement data during treatment of the patient, as described above with reference to FIG. 3. In an aspect, the measurement data may be initially received by the electronic device associated with the patient (or guardian) and then transmitted to the electronic device of the medical professional. At step 1130, the method 1100 includes analyzing the resistance force measurement data to determine whether the treatment is being provided correctly. For example, the analyzing may include comparing the resistance force measurement data to the resistance force levels indicated in the configuration information to determine whether the measured resistance force levels exceed the resistance force levels configured for the patient's treatment. The analyzing may also include determining whether the patient receives appropriate levels of treatment for the amount of time and at the frequency specified in the configuration information. It is noted that other types of analysis may also be performed based on the received resistance force measurement data.

The method 1100 may include, at step 1140, generating one or more notifications or alerts based on the analyzing. For example, where the analyzing indicates the amount of resistance force is greater than the amount of resistance force specified in the configuration information, an alert may be generated to notify the medical professional and/or the patient that the wearable article may be configured improperly, as described above. Additionally, where the analyzing indicates that the patient is not receiving treatment at the appropriate frequency or for the appropriate amount of time during each treatment session, an alert may be generated to notify the medical professional and/or patient that the treatment plan is not being followed correctly. It is noted that other types of alerts or notifications may be generated and transmitted and that the exemplary alerts/notifications described above have been provided for purposes of illustration, rather than by way of limitation.

It is noted that although the embodiments described above have been described with respect to treatment of certain human conditions, such as proprioceptive dysfunction or vestibular disorders, embodiments are not limited to such applications. Many sports related activities involved specialized movements, such as a golf swing, a tennis swing, and wearable articles in accordance with the present disclosure may be applied to such activities. For example, a shirt may be provided with one or more resilient members designed to train and strengthen a user's muscles in a manner specifically targeting a certain type of movement. Through repetition, the resilient members of such a wearable article may retrain or enhance the user's motion during such activities, thereby improving the user's ability to perform at a high level for the particular sports application of interest to the user. Other examples of sports for which wearable articles may be provided in accordance with the present disclosure may include running, football (e.g., placekicking or punting a football, throwing a football, etc.), ice skating, cross country skiing, and the like. Thus, it is noted that while a majority of the present disclosure is described in relation to providing treatment to a patient, wearable articles configured according to the concepts disclosed herein may also be used as training devices configured to teach users particular types of motions (e.g., a golf swing, a tennis swing, a throwing motion, etc.) relevant to athletes or for other purposes.

For example, and referring to FIG. 12, a block diagram illustrating a wearable article configured in accordance with embodiments of the present disclosure for training a gold swing is shown. As shown in FIG. 12, the wearable article may be embodied as a long sleeve shirt having a torso portion 1210, a first limb portion 1212, and a second limb portion 1214. The first limb portion 1212 may correspond to a left arm portion of the long sleeve shirt and the second limb portion 1214 may correspond to a right arm portion of the long sleeve shirt. The wearable article also includes a resilient member 1216 that extends from a distal end of the first limb portion 1212 do a distal portion of the second limb portion 1214. The resilient member 1216 bisects the arm at the mid-point of resistance, which may facilitate training designed to achieve an optimal swing pattern. The anchor point(s) of the resilient member 1216 may take several forms, one being around the opposite shoulder, the second aligned with each arm in appropriate line and also each arm could be wrapped around the torso. For example, as shown in FIG. 12, the resilient member 1216 may run along the back of the user's right arm (e.g., as shown in the back view with respect to limb portion 1214) towards the should and middle of the user's upper back and then across the back and towards the user's left armpit and then wraps from underneath the user's left armpit around the user's left arm and meets the distal end of the limb portion 1212 approximate a midpoint of the distal end of the limb portion 1212. The resilient member 1216 may be configured to provide consistent resistance during training in a manner that promotes muscle memory and provides even muscle contraction throughout the swing. As described above, the resilient member 1216 may be disposed within a resilient member channel and may utilize one or more cord locks and/or resistance level indicators and/or limiters to control the amount of resistance force provided. Wrist or hand straps 1218, 1220 may be provided to prevent the limb portions from rising up the user's arm during training. It is noted that the exemplary aspects of the wearable article illustrated in FIG. 12 have been provided for purposes of illustration, rather than by way of limitation and that other wearable articles configured to provide training for specific aspects of a sport or for other rehabilitation purposes may readily be recognized from the present disclosure. Accordingly, the concepts disclosed herein are not to be limited to the specific examples disclosed herein.

Although the embodiments of the present disclosure and their advantages have been described in detail, it should be understood that various changes, substitutions and alterations can be made herein without departing from the spirit and scope of the disclosure as defined by the appended claims. Further, although the drawings may illustrate some of the concepts disclosed herein as logical or functional blocks, it is to be understood that each of those blocks may be implemented in hardware, software, or a combination of hardware and software. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A wearable article comprising:
    a first limb section;
    a second limb section;
    a body section joining the first limb section and the second limb section;
    one or more resilient members, wherein a first resilient member of the one or more resilient members spans a length of at least a portion of the first limb section and is configured to provide a first resistance force during movement of at least the first limb section;
    one or more cord locks, wherein a first cord lock of the one or more cord locks corresponds to the first resilient member and is configured to slideably engage the first resilient member, wherein the slideable engagement of the first cord lock with the first resilient member is configured to adjust the first resistance force provided by the first resilient member during movement of at least the first limb section;
    one or more electronic strain gauges configured to measure the resistance force provided by each of the one or more resilient members, wherein a first electronic strain gauge of the one or more electronic strain gauges is coupled to a first end of the first resilient member and the first cord lock is proximate a second end of the first resilient member; and
    a communication interface communicatively coupled to the one or more electronic strain gauges and configured to:
        receive information representative of at least one resistance force measured by the one or more electronic strain gauges; and
        transmit the information to a remote device via a wireless communication link.

2. The wearable article of claim 1, wherein the first resilient member provides the first resistance force when the first cord lock slideably engages the first resilient member at a first location and a second amount of resistance force when the first cord lock slideably engages the first resilient member at a second location.

3. The wearable article of claim 1, wherein the remote device comprises a user device, and wherein the user device presents the information representative of at least one resistance force measured by the one or more electronic strain gauges to a user.

4. The wearable article of claim 1, wherein each resilient member of the one or more resilient members comprises a plurality of visual indicators, each visual indicator of the plurality of visual indicators corresponding to a particular amount of resistance force, and wherein the plurality of visual indicators identify locations for slideably engaging a corresponding cord lock to provide a particular amount of resistance force.

5. The wearable article of claim 1, wherein the first resilient member is configured to train muscles of a user wearing the wearable article to perform a particular movement.

6. The wearable article of claim 5, wherein the particular movement comprises a sports movement.

7. The wearable article of claim 5, wherein the particular movement is configured to strengthen the muscles of the user used during the particular movement.

8. The wearable article of claim 1, wherein the first limb section, the second limb section, and the body section are configured according to physical characteristics of a user wearing the wearable article.

9. The wearable article of claim 1, wherein the one or more resilient members includes a plurality of resilient members that includes the first resilient member, and wherein a second resilient member of the plurality of resilient members spans at least a portion of the second limb section.

10. The wearable article of claim 1, wherein the first resilient member wraps at least partially around the first limb section.

11. The wearable article of claim 1, wherein at least one of the one or more resilient members is anchored on the body section.

12. A method comprising:
provide a wearable article comprising:
a first limb section;
a second limb section;
a body section joining the first limb section and the second limb section;
one or more resilient members, wherein a first resilient member of the one or more resilient members spans a length of at least a portion of the first limb section and is configured to provide a first resistance force during movement of at least the first limb section;
one or more cord locks, wherein a first cord lock of the one or more cord locks corresponds to the first resilient member and is configured to slideably engage the first resilient member, wherein the slideable engagement of the first cord lock with the first resilient member is configured to adjust the first resistance force provided by the first resilient member during movement of at least the first limb section;
one or more electronic strain gauges configured to measure the resistance force provided by each of the one or more resilient members, wherein a first electronic strain gauge of the one or more electronic strain gauges is coupled to a first end of the first resilient member and the first cord lock is proximate a second end of the first resilient member; and
a communication interface communicatively coupled to the one or more electronic strain gauges;
transmitting, by the communication interface, information representative of at least one resistance force measured by the one or more electronic strain gauges to a remote device;
receiving, by one or more processors of the remote device, the information representative of at least one resistance force measured by the one or more electronic strain gauges; and
presenting, by the one or more processors of the remote device, the information at a display of the remote device.

13. The method of claim 12, further comprising determining, by the one or more processors of the remote device, whether the first cord lock is slideably engaged with the first resilient member at a correct location based on whether the information representative of at least one resistance force measured by the one or more electronic strain gauges.

14. The method of claim 12, further comprising generating, by the one or more processors of the remote device, an alert when the first resistance force does not match a predetermined amount of resistance force to within a threshold tolerance, wherein the first resistance force is included in the information representative of at least one resistance force measured by the one or more electronic strain gauges.

15. The method of claim 12, further comprising tracking the first resistance force over time.

16. The method of claim 15, further comprising:
comparing information associated with the first resistance force tracked over time to a treatment schedule; and
validating compliance with the treatment schedule based on the comparing.

17. The method of claim 12, wherein the information representative of at least one resistance force measured by the one or more electronic strain gauges comprises a second resistance force produced by a second resilient member of the one or more resilient members and measured by a second electronic strain gauge of the one or more electronic strain gauges, the second electronic strain gauge corresponding to the second resilient member.

18. The method of claim 12, wherein the first resilient member is configured to train muscles of a user wearing the wearable article to perform a particular movement.

19. The method of claim 18, wherein the particular movement comprises a sports movement.

20. The method of claim 19, wherein the sports movement comprises a movement selected from the list comprising: a running motion, a throwing motion, a skating motion, a skiing motion, a kicking motion, and a swinging motion.

* * * * *